US011479617B2

(12) United States Patent
Sydlik et al.

(10) Patent No.: US 11,479,617 B2
(45) Date of Patent: Oct. 25, 2022

(54) CHELATOR-FUNCTIONALIZED GLYCOSAMINOGLYCANS

(71) Applicants: Carnegie Mellon University, Pittsburgh, PA (US); University of Connecticut, Farmington, CT (US)

(72) Inventors: Stefanie A. Sydlik, Pittsburgh, PA (US); Anne M. Arnold, Pittsburgh, PA (US); Brian D. Holt, Pittsburgh, PA (US); Cato T. Laurencin, Avon, CT (US); Leila Daneshmandi, Manchester, CT (US); Stephen Schmidt, Pittsburgh, PA (US)

(73) Assignees: Carnegie Mellon University, Pittsburgh, PA (US); University of Connecticut, Farmington, CT (US)

( * ) Notice: Subject to any disclaimer, the term of this patent is extended or adjusted under 35 U.S.C. 154(b) by 0 days.

(21) Appl. No.: 16/552,774

(22) Filed: Aug. 27, 2019

(65) Prior Publication Data
US 2020/0062869 A1 Feb. 27, 2020

Related U.S. Application Data

(60) Provisional application No. 62/921,981, filed on Jul. 17, 2019, provisional application No. 62/765,479, filed on Aug. 27, 2018.

(51) Int. Cl.
| C08B 37/08 | (2006.01) |
| C08B 37/00 | (2006.01) |
| A61K 31/728 | (2006.01) |
| C08K 3/08 | (2006.01) |
| C08K 5/23 | (2006.01) |
| A61L 27/54 | (2006.01) |
| C08K 5/17 | (2006.01) |

(52) U.S. Cl.
CPC ........ *C08B 37/0072* (2013.01); *A61K 31/728* (2013.01); *A61L 27/54* (2013.01); *C08B 37/0069* (2013.01); *C08K 3/08* (2013.01); *C08K 5/175* (2013.01); *C08K 5/235* (2013.01); C08K 2003/0843 (2013.01); C08K 2003/0862 (2013.01)

(58) Field of Classification Search
CPC ............ C08B 37/0072; C08B 37/0069; A61K 31/728; A61K 9/00; A61K 47/61
See application file for complete search history.

(56) References Cited

U.S. PATENT DOCUMENTS

| 5,401,491 | A | 3/1995 | Sadler et al. |
| 5,707,604 | A | 1/1998 | Ranney et al. |
| 7,605,166 | B2 | 10/2009 | Yednock et al. |
| 8,716,204 | B2 | 5/2014 | Stark et al. |
| 8,790,714 | B2 | 7/2014 | Amador et al. |
| 9,901,543 | B2 | 2/2018 | Chausson et al. |
| 2006/0078500 | A1 | 4/2006 | Neeman et al. |
| 2007/0160680 | A1 | 7/2007 | Schwenke |
| 2009/0092664 | A1 | 4/2009 | Mumper et al. |

FOREIGN PATENT DOCUMENTS

| EP | 0055028 | 6/1982 |
| JP | 4813179 | 11/2011 |

OTHER PUBLICATIONS

Vilensky et al., Ann. Emerg. Med., 2003, 41, p. 378-383. (Year: 2003).*
Altman et al., "Intraarticular sodium hyaluronate (Hyalgan) in the treatment of patients with osteoarthritis of the knee: a randomized clinical trial. Hyalgan Study Group," J Rheumatol., 1998, 25(11):2203-2212.
Berber et al., "Management of metal-on-metal top implant patients: Who, when and how to revise?" World J Orthop., 2016, 7(5):272-279.
Curran, "Hyaluronic acid (Supartz®): a review of its use in osteoarthritis of the knee," Drugs Aging, 2010, 27(11):925-941.
Ellman's Test Protocol.
Giampreti et al., "N-Acetyl-Cysteine as Effective and Safe Chelating Agent in Metal-on-Metal Hip-Impianted Patients: Two Cases," Case Reports in Orthopedics, 2016, 2016:1-7.
Green et al., "Neuropsychiatric symptoms following metal-on-metal implant failure with cobalt and chromium toxicity," BMC Psychiatry, 2017, 17:33.
Hartmann et al., "Metal Ion Concentrations in Body Fluids after Implantation of Hip Replacements with Metal-on-Metal Bearing—Systematic Review of Clinical and Epidemiological Studies," PLoS One., 2013, 8(8):e70359.
Husain, "Theoretical Basis of Analysis: Complexometric Titrations," Lecture by Dr. Asif Husain, Dept. of Pharmacuetical Chemistry, New Delhi, Aug. 8, 2007.
Joint Replacement Surgery: Health Information Basics for You and Your Family.
Longcope et al., "The use of BAL (British Anti-Lewisite) in the treatment of the injurious effects of arsenic, mercury and other metallic poisons," Ann. Intern. Med., 1949, 31(4):545-54.
Nawabi et al., "Magnetic resonance imaging findings in symptomatic versus asymptomatic subjects following metal-on-metal hip resurfacing arthroplasty," J Bone Joint Surg, Am., 2013, 95(10):895-902.
Neustadt et al., "Clinical effects of intraarticular injection of high molecular weight hyaluronan (Orthovisc) in osteoarthritis of the knee: a randomized, controlled, multicenter trial," J Rheumatol., 2005, 32(10):1928-1936.
Oliveira et al., "Metallosis: A diagnosis not only in patients with metal-on-metal prostheses," Eur. J Radiology Open, 2015, 2:3-6.

(Continued)

Primary Examiner — Jonathan S Lau
(74) Attorney, Agent, or Firm — Fish & Richardson P.C.

(57) ABSTRACT

A compound includes a polysaccharide moiety and one or more chelating agents. The one or more chelating agents are covalently bonded to the polysaccharide moiety. The polysaccharide moiety can include a glycosaminoglycan moiety, such as a hyaluronic acid polymer or a sulfated glycosaminoglycan moiety. The compound can be used to treat or prevent a disease or disorder in a patient with a metal implant. The compound reduces a concentration of metal particulates or metal ions in the subject.

19 Claims, 20 Drawing Sheets

(56) References Cited

OTHER PUBLICATIONS

PCT International Search Report and Written Opinion in International Appln. No. PCT/US2019/048376, dated, Jan. 2, 2020, 16 pages.
Pritchett, "Adverse reaction to metal debris: metallosis of the resurfaced hip," Curr. Orthop. Pract., 2012, 23(1):50-58.
Revell et al., "Metal Concentration in Synovial Fluids of Patients with prosthetic knee arthroplasty," Clinical Orthopaedics and Related Research, 1982, 170:169-174.
Sampson et al., "Clinical usefulness of blood metal measurements to assess the failure of metal-on-metal hip implants," Ann. Clin. Biochem., 2012, 49(2):118-131.
Sharma et al., "Biomedical Implications of Heavy Metals Induced Imbalances in Redox Systems," BioMed Res. Int., 2014, 1-26.
Silverman et al., "Metal-on-metal total hip arthroplasty: is there still a role in 2016?" Curr. Rev. Musculoskelet. Med., 2016, 9(1):93-96.
Smet et al., "Metal ion measurement as a diagnostic tool to identify problems with metal-on-metal hip resurfacing," J Bone Joint Surg. Am., 2008, 90(Suppl 4):202-208.
Song et al., "Prosthesis Infections after Orthopedic Joint Replacement: The Possible Role of Bacterial Biofilms," Orthop. Rev., 2013, 5(2):e14.
Teo et al., "Metal Hypersensitivity Reactions to Orthopedic Implants," Dermatol. Ther., 2017, 7(1)53-64.
Thomas, "Clinical and diagnostic challenges of metal implant allergy using the example of orthopaedic surgical implants," Allergo J Int., 2014, 23(6): 179-185.
Total Joint Replacement—Orthoinfo—AAOS.
Ueno, "Protective effects of thiol containing chelating agents against liver injury induced by hexavalent chromium in mice," Kitasato Arch. Exp. Med., 1992, 65(2-3):87-96.
Verma et al., "New colorimetric and photometric titration procedures for the determination of Dimercaprol in injections," Indian J Pharm. Sci., 1995, 57:249-251.
International Preliminary Report on Patentability in International Application No. PCT/US2019/048376, dated Mar. 2, 2021, 8 pages.
Bertrand et al., "New pharmaceutical applications for macromolecular binders," Journal of Controlled Release, Oct. 2011, 155(2):200-210.

* cited by examiner

CHELATOR-FUNCTIONALIZED GLYCOSAMINOGLYCANS

CLAIM OF PRIORITY

This application claims priority under 35 U.S.C. § 119(e) to U.S. Provisional Application Ser. No. 62/765,479, filed on Aug. 27, 2018, and U.S. Provisional Application Ser. No. 62/921,981 entitled "Dimercaprol Functionalized Glycosaminoglycans: Cytocompatible, Synovial Fluid Mimicking Polymeric Systems that Chelate Cobalt, Nickel, and Chromium", filed on Jul. 17, 2019, the entire contents of each of which are hereby incorporated by reference.

TECHNICAL FIELD

This document relates to compositions and methods for chelation therapy. More specifically, this document relates to compounds comprising glycosaminoglycans and chelators.

BACKGROUND

Millions of patients worldwide have metal implants, such as metal-on-metal (MoM) or metal-on-polyethylene (MoP) implants that, unfortunately, are failing due to the significantly increased generation of heavy metal ions, including cobalt, nickel, and chromium ions. These implants' unique wear causes adverse effects in patients, and one of the worst pathologies is metallosis which is characterized by localized aseptic fibrosis, necrosis, bone deterioration, implant loosening, and extreme pain, in addition to neurological damage, carcinogenesis, and mortality. Currently, revision surgeries are required to remove the metal implants, but these procedures are highly invasive, painful, pose substantial risk to the patient, costly, and may not be feasible due to patient comorbidities.

SUMMARY

The compounds and therapeutic compositions described herein include materials for chelation therapy, such as to treat or prevent metallosis in humans. The compounds, also referred to as "chelating compounds", comprise a polysaccharide moiety covalently bound to one or more chelating agents. In some implementations, dimercaprol (British anti-Lewisite, or BAL) is covalently attached to hyaluronic acid (HA) polymers. The resulting polymeric chelator (BAL-HA) chelates metals in therapeutically relevant concentrations. Other chelators include, but are not limited to, ethylene diamine tetra-acetic acid (EDTA), N-acetyl-cysteine (NAC), D-penicillamine, 1,4,7-triazacyclononanetriacetic acid (NOTA), 1,4,7,10-tetraazacyclododecane-1,4,7,10-tetraacetic acid (DOTA), 1,4,7-triazacyclononane-1-glutaric acid-4,7-diacetic acid (NODAGA), diethylene triaminepentaacetic acid (DTPA), cyclohexyl-1,2-diaminetetraacetic acid (CDTA), ethyleneglycol-O,O'-bis(2-aminoethyl)-N,N, N',N'-tetraacetic acid (EGTA), N,N-bis (hydroxybenzyl)-ethylenediamine-N,N'-diacetic acid (HBED), triethylene tetramine hexaacetic acid (TTHA), hydroxyethyidiamine triacetic acid (HEDTA), 1,4,8,11-tetraazacyclotetradecane-N,N', N'',N'''-tetraacetic acid (TETA), and 1,4,7,10-tetraaza-1,4,7,10-tetra-(2-carbamoyl methyl)-cyclododecane (TCMC). Polysaccharide moieties include glycosaminoglycans, including but not limited to hyaluronic acid polymers and sulfated glycosaminoglycan moieties (e.g. chondroitin sulfate (CS)), and other polysaccharides including, for example, glycogen, chitin, and cellulose.

The compounds described in this document are useful to treat or prevent diseases or disorders including, without limitation, diseases and disorders associated with abnormally high levels of metal in patients, or otherwise remove metal ion particles or debris from a site of treatment (e.g., a joint space, a non-joint space, etc.). For example, the chelating compound can be used to treat metallosis, allergies (including metal hypersensitivity), heavy metal poisoning, hard metal pneumoconiosis (occupational exposure), vineyard sprayers lung (occupational exposure), soft tissue inflammatory reactions, chronic inflammation, pseudotumors, aseptic lymphocytic vasculitis associated-lesion (AL-VAL), bursae, adverse reactions to metal debris (ARMD), implant loosening, osteolysis, and metabolic conditions associated with undesired levels of metals (including Wilson's disease, haemosiderosis, and haemochromatosis).

The implementations described herein can provide various benefits. For instance, the compounds and methods described herein permit treatment or prevention of diseases and disorders associated with undesired levels of metal in a patient including, without limitation, metallosis. For example, in some treatments, the chelating compound can reduce effects of metallosis resulting from degradation of metal implants, such as metal-on-metal (MoM) or metal-on-polyethylene (MoP) implants. In some examples, the chelating compounds are useful to remove or reduce the level of metal in the body that has been introduced in some other way. The chelating compounds with attached metal can then be removed from the treatment site (e.g., by flushing). In other examples, the chelating compounds with attached metal are resorbed and then safely processed by the body.

In some implementations, the treatment site can include a joint space, such as an articulating joint space, a non-articulating joint space, a synovial joint space, or a non-synovial joint space. For example, in some implementations the chelating compound can be used for orthopedic treatments. For example, the chelating compound can be administered into an intra-articular space (e.g., in a hip joint, knee joint, spine, ankle, etc.) to remove metal from the intra-articular space. In some examples, the chelating compounds with attached metal can be flushed away or otherwise removed after a period of time period to allow for chelation in patients with metallosis.

In some implementations, the treatment site can include a non-joint space, or a space in which no joint is present. For example, the treatment site can include a blood vessel, a heart, a spinal canal, an epidural space, a subcutaneous space, a ventricular space, a uterus, a portion of an alimentary canal, an intraosseous space, a brain, and so forth.

In an aspect, more than 2.9 million joint replacement procedures are conducted annually to alleviate pain and restore physiological movement in patients suffering from disease, age, and injury related traumas. Joint replacement entails either the partial or whole removal of a dysfunctional joint that is replaced by a non-resorbable prosthetic implant. Prostheses are most commonly composed of metal alloys containing titanium, molybdenum, cobalt, chromium, or nickel that remain as permanent fixtures over the lifetime of the patient. Thus, implant longevity is a critical factor for joint prostheses since revision surgeries are invasive, painful, and increase the risk of infection. Considering this, significant focus has centered on improving the durability of joint prostheses to reduce implant wear and failure.

MoM implants, which contain a ball and socket component composed of metal, were popularized due to their low wear rate in vitro. However, after several years, MoM implants have demonstrated higher wear and failure rates in vivo than previous implant models. While having less volumetric wear, MoM implant wear results in a buildup of significantly more, smaller sized metal particulates and solubilized ions. One pathology that is a consequence of this different wear is metallosis: localized and systemic distribution of heavy metal ions. Metallosis poses significant health concerns for the patient and can be characterized by localized aseptic fibrosis, necrosis, bone deterioration, implant loosening, and extreme pain. Systemic distribution of toxic metal ions can also cause neurological damage, carcinogenesis, and death.

Metallosis due to implant wear can be difficult to diagnose since many clinicians rely on quantitative analysis of metal ions in serum. Studies have shown that metal concentrations in serum do not always correlate with implant wear and are poor indicators of metallosis; therefore, metallosis is usually diagnosed after the emergence of symptoms, which can occur years after the prostheses has begun to fail. Currently, treatments for metallosis due to implant wear are limited to revision surgery. Revision surgery effectively removes the implant and localized metals. However, revision surgery is a serious medical procedure with associated risks to the patients and substantial healthcare costs and does not address solubilized metals in the body that pose significant toxicity risks. Since several million patients worldwide have MoM prostheses, there is a clinical need to address heavy metal ions due to implant wear.

To overcome the above problems, treatment using the chelating compound described in this disclosure is configured to extract these metal ions or other debris from the body and prevent or reduce the effects of metallosis. For the sake of brevity, the term "metal" will be used to collectively refer to free metal ions or metal ions bound to low affinity ligands (e.g., citrate), as well as metal ion debris and metal particles or other forms of metal capable of being chelated. In some implementations the metal is a metal selected from groups 3 through 12 on the periodic table. In some implementations the metal is one or more of As, Hg, Au, Pb, Co, Ni, Cr, Ti, Ta, Cu, Fe, Mo, and Gd. In some implementations the metal is one or more of Co, Ni, and Cr.

In an aspect, the chelating compound includes glycosaminoglycans (GAGs) such as hyaluronic acid (HA) and chondroitin sulfate (CS) modified with dimercaprol, also known as British anti-Lewisite (BAL), a small molecule chelating agent. The BAL-HA and BAL-CS systems can serve as synovial fluid mimics that also retain the ability to chelate cobalt, nickel, and chromium ions while reducing the toxicity of unmodified BAL. The polymeric systems are cytocompatible and can chelate metal in therapeutically relevant concentrations, indicating their potential as an injectable therapeutic for localized treatment of metallosis due to implant wear in joint and non-joint areas. Thus, this invention could extend the lifetime of metal-containing implants that have already been implanted by removing toxic solubilized metals in joint cavities.

Similarly, as previously indicated, the chelating compounds described in this disclosure can be used to remove excess or undesired metal from non-joint spaces of the patient. For example, degradation of a metal stent that causes excess levels of metal ions and debris in a vascular region of the patient can be similarly treated by administering the chelating compound to remove the excess metal from the region.

In an aspect, a compound includes a polysaccharide moiety and one or more chelating agents. Generally, the one or more chelating agents are covalently bonded to the polysaccharide moiety. In some implementations, each of the chelating agents is independently a chelator of one or more metals selected from the group including As, Hg, Au, Pb, Co, Ni, Cr, Ti, Ta, Cu, Fe, Mo, and Gd. In some implementations, each of the chelating agents is independently a chelator of one or more metals selected from the group including Co, Ni, and Cr.

In some implementations, each of the chelating agents is independently selected from the group including British anti-Lewisite (BAL) dimercaprol, ethylene diamine tetraacetic acid (EDTA), N-acetyl-cysteine (NAC), D-penicillamine, 1,4,7-triazacyclononanetriacetic acid (NOTA), 1,4,7,10-tetraazacyclododecane-1,4,7,10-tetraacetic acid (DOTA), 1,4,7-triazacyclononane-1-glutaric acid-4,7-diacetic acid (NODAGA), diethylene triaminepentaacetic acid (DTPA), cyclohexyl-1,2-diaminetetraacetic acid (CDTA), ethyleneglycol-O, O'-bis(2-aminoethyl)-N, N, N', N'-tetraacetic acid (EGTA), N, N-bis(hydroxybenzyl)-ethylenediamine-N, N'-diacetic acid (HBED), triethylene tetramine hexaacetic acid (TTHA), hydroxyethyidiamine triacetic acid (HEDTA), 1,4,8,11-tetraazacyclotetradecane-N, N', N'', N'''-tetraacetic acid (TETA), and 1,4,7,10-tetraaza-1,4,7,10-tetra-(2-carbamoyl methyl)-cyclododecane (TCMC).

In some implementations, each of the chelating agents is independently selected from the group including dimercaprol, ethylene diamine tetra-acetic acid (EDTA), N-acetyl-cysteine (NAC), and D-penicillamine. In some implementations, each of the chelating agents are the same. In some implementations, the chelating agent is dimercaprol.

In an aspect, the polysaccharide moiety is selected from the group including a glycosaminoglycan moiety. In some implementations, the glycosaminoglycan moiety is selected from the group including a hyaluronic acid polymer and a sulfated glycosaminoglycan moiety. In some implementations, the glycosaminoglycan moiety is a hyaluronic acid polymer.

In an aspect, the compound comprises about 1:1 to about 1:3 chelator to repeat unit of the hyaluronic acid polymer. In some implementations, the compound comprises about 1:1 chelator to repeat unit of the hyaluronic acid polymer.

In some implementations, the glycosaminoglycan moiety is a sulfated glycosaminoglycan moiety. In some implementations, the glycosaminoglycan moiety is chondroitin sulfate. In some implementations, the compound comprises about 1:1 to about 1:3 chelator to repeat unit of the chondroitin sulfate. In some implementations, the compound comprises about 1:1 chelator to repeat unit of the chondroitin sulfate. In some implementations, the glycosaminoglycan moiety is hyaluronic acid and the chelating agent is dimercaprol.

In an aspect, a pharmaceutical composition includes a compound having a polysaccharide moiety and one or more chelating agents, and a pharmaceutically acceptable carrier. In some implementations, the pharmaceutically acceptable carrier comprises water. In some implementations, the composition is formulated as an injectable hydrogel.

In an aspect, a process for preventing a disease or disorder includes administering a therapeutically effective amount of a compound having a polysaccharide moiety and one or more chelating agents to the joint of the patient. In an aspect, a process includes administering a therapeutically effective amount of a compound having a polysaccharide moiety and one or more chelating agents to the site of the metal implant. In some implementations, the disease or disorder is associated with abnormally high levels of metal in the patient. In some implementations, the disease or disorder is associated with abnormally high levels of metal particulates, abnormally high levels of metal ions, or a combination thereof, in the patient. In some implementations, the process includes reducing a concentration of metal particulates or metal ions in the subject. In some implementations, the disease or disorder is selected from the group including metallosis, allergies (including metal hypersensitivity), heavy metal poisoning, hard metal pneumoconiosis (occupational exposure), vineyard sprayers lung (occupational exposure), soft tissue inflammatory reactions, chronic inflammation, pseudotumors, aseptic lymphocytic vasculitis associated-lesion (ALVAL), bursae, adverse reactions to metal debris (ARMD), implant loosening, osteolysis, and metabolic conditions associated with undesired levels of metals (including Wilson's disease, haemosiderosis, and haemochromatosis). In some implementations, the disease or disorder is metallosis.

In an aspect, the metal implant is an implant selected from the group including a hip implant, a knee implant, a shoulder implant, a wrist implant, a vertebral implant, an ankle implant, and an elbow implant. In some implementations, the patient has an implant selected from the group including a stent, a mesh, electrodes, and biosensors. In some implementations, the metallosis is associated with degradation of the metal implant in the patient. In an aspect, the metal is selected from the group including As, Hg, Au, Pb, Co, Ni, Cr, Ti, Ta, Cu, Fe, Mo, and Gd. In some implementations, the metal is selected from the group including Co, Ni, and Cr. In some implementations, the administration is parenteral administration.

In some implementations, the compound is administered to a site localized at the metal implant in the patient. In some implementations, the metal implant includes a metal-on-metal implant. The metal implant includes a metal-on-polyethylene implant. In some implementations, the site is selected from the group including a blood vessel, a heart, a spinal canal, an epidural space, a subcutaneous space, a ventricular space, the uterus, a portion of an alimentary canal, an intraosseous space, and a brain. In some implementations, following the administration of the therapeutically effective amount of the compound, the process includes flushing the site with a wash solution including hyaluronic acid dissolved in saline.

The details of one or more embodiments are set forth in the accompanying drawings and the description below. Other features and advantages will be apparent from the description and drawings, and from the claims.

DETAILED DESCRIPTION

Figure 1A:
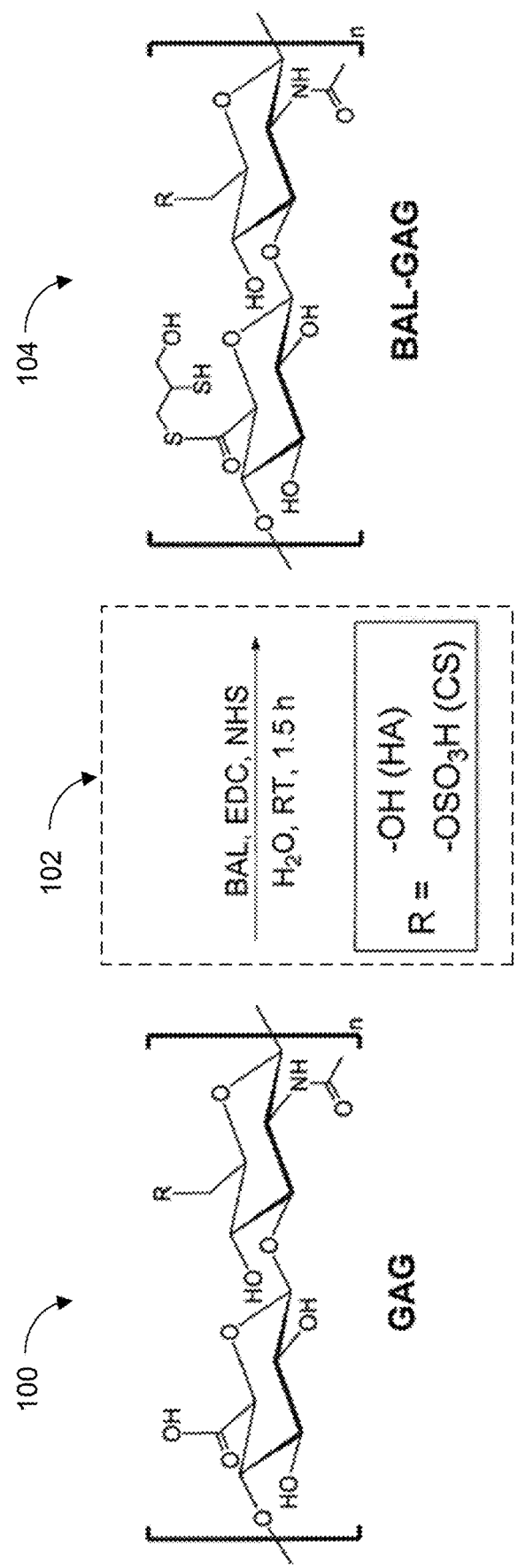
FIG. 1A is a diagram of an example chelating compound.
Figure 1B:
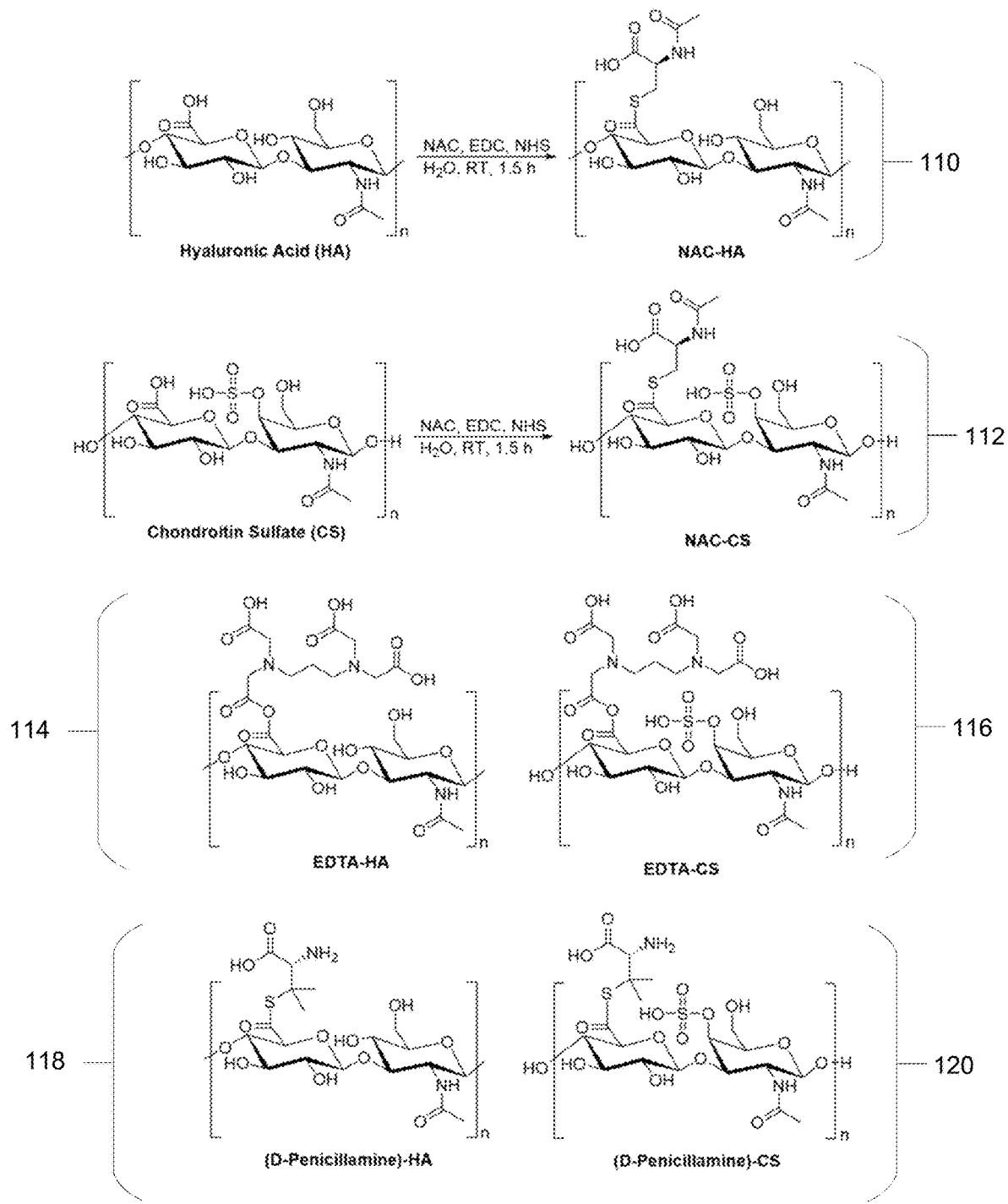
FIG. 1B shows diagrams of example chelating compounds.

FIGS. 1A-1B show examples of a chelating compound. The chelating compound mimics the composition of synovial fluid while simultaneously chelating toxic metals from joint cavities deposited from prosthetic metal implant wear. In one example, a chelating compound 104 of FIG. 1A uses carbodiimide coupling chemistry (shown in box 102) to activate carboxylic acid functional groups of GAGs 100, such as hyaluronic acid (HA) and chondroitin sulfate (CS), to promote covalent coupling of BAL to the polymeric backbone. The BAL functionalized GAGs that form chelating compound 104 represent a metal-chelating polymeric system that chelates cobalt, nickel, and chromium in therapeutically relevant concentrations.

Generally, the chelating compound includes a polysaccharide moiety and one or more chelating agents. A non-limiting example of the polysaccharide moiety is a glycosaminoglycan (GAG) moiety. While the GAG moiety is subsequently described in detail, other similar polysaccharide moieties are possible, including, but not limited to hyaluronic acid polymers and sulfated glycosaminoglycan moieties (e.g. chondroitin sulfate (CS)), and other polysaccharides including, for example, glycogen, chitin, and cellulose. Additionally, while HA and CS are two examples described for activating the carboxylic acid functional groups of the GAG, other glycosaminoglycan moieties can be used.

The chelating compound includes a chelating agent that is bonded to the polysaccharide moiety. In some implementations, the chelating agent (or plurality of chelating agents) is/are bonded to the polysaccharide moiety by covalent bond(s). Chelating agents include, without limitation, British anti-Lewisite (BAL) dimercaprol, ethylene diamine tetra-acetic acid (EDTA), N-acetyl-cysteine (NAC), D-penicillamine, 1,4,7-triazacyclononanetriacetic acid (NOTA), 1,4,7,10-tetraazacyclododecane-1,4,7,10-tetraacetic acid (DOTA), 1,4,7-triazacyclononane-1-glutaric acid-4,7-diacetic acid (NODAGA), diethylene triaminepentaacetic acid (DTPA), cyclohexyl-1,2-diaminetetraacetic acid (CDTA), ethyleneglycol-O,O'-bis(2-aminoethyl)-N,N,N', N'-tetraacetic acid (EGTA), N,N-bis(hydroxybenzyl)-ethylenediamine-N,N'-diacetic acid (HBED), triethylene tetramine hexaacetic acid (TTHA), hydroxyethyidiamine triacetic acid (HEDTA), 1,4,8,11-tetraazacyclotetradecane-N,N',N",N"'-tetraacetic acid (TETA), and 1,4,7,10-tetraaza-1,4,7,10-tetra-(2-carbamoyl methyl)-cyclododecane (TCMC).

FIG. 1B shows diagrams 110, 112, 114, 116, 118, and 120 of additional chelating compounds. Diagram 110 shows an example of NAC-HA. Diagram 112 shows an example of NAC-CS. Diagram 114 shows an example of EDTA-HA. Diagram 116 shows an example of EDTA-CS. Diagram 118 shows an example of D-penicillamine-HA. Diagram 120 shows an example of D-penicillamine-CS The chelating agents of the chelating compound permit the binding and subsequent removal of metal from a treatment site. The treatment site includes an area in the patient in which the chelating compound is applied to remove excess metal. Generally, the treatment site includes the area near a metal implant that can be affected by degradation of the metal implant. For example, the treatment site can include a joint or a non-joint space. A joint space refers to a treatment site including a joint. A non-joint space refers to a treatment site that does not include a joint. The chelating compound allows the removal of metal from the treatment site. The metals can include one or more metals selected from the group consisting of As, Hg, Au, Pb, Co, Ni, Cr, Ti, Ta, Cu, Fe, Mo, and Gd. In some implementations, the chelating agents remove one or more of Co, Ni, and Cr. The size of the metal particles can be varied. For example, the size can be as small as individual ions and as large as 500 nm in diameter or more.

The chelating compound can include various ratios of chelating agent to the polysaccharide polymer. For example, for chelating compounds including the HA polymer, a ratio of the chelator to repeat unit of the hyaluronic acid polymer can be between about 1:1 to about 1:3. In some implementations, for chelating compounds including the chondroitin sulfate, a ratio of the chelator to repeat unit of the chondroitin sulfate can be between about 1:1 to about 1:3. However, while these ratios can be different for different chelators, functionalization efficiency of the chelator can be used to predict the approximate ratio of chelator to repeat unit. For example, the range of ratios is generally between 1:1 chelator:GAG to 1:5 chelator:GAG.

Various combinations of the chelating agent and the glycosaminoglycan moiety are possible. For example, in some implementations, the glycosaminoglycan moiety is hyaluronic acid and the chelating agent is dimercaprol. In some implementations, the glycosaminoglycan moiety is chondroitin sulfate and the chelating agent is dimercaprol.

The chelating compounds can be included in a pharmaceutical composition. These pharmaceutical compositions can be prepared as described herein or elsewhere, and can be administered by a variety of routes, depending upon whether local or systemic treatment is desired and upon the area to be treated. In some implementations, the administration is parenteral. Parenteral administration includes, for example, intravenous, intraarterial, intradermal, subcutaneous, intraperitoneal, intramuscular injection or infusion; or intracranial administration, (e.g., intrathecal or intraventricular, administration). Parenteral administration can be in the form of a single bolus dose, or may be, for example, by a continuous perfusion pump. In some implementations, the compounds and pharmaceutical compositions provided herein are suitable for parenteral administration. In some implementations, the pharmaceutical compositions provided herein are suitable for intravenous administration. In some implementations the pharmaceutical compositions are administered using one or more microneedles. Conventional pharmaceutical carriers, aqueous, powder or oily bases, thickeners and the like may be necessary or desirable. In some implementations, the chelating compound is formulated as an injectable hydrogel. In some implementations, the pharmaceutical compositions provided herein are suitable for chelating compound other modes of administration, including, without limitation, oral ingestion, using a pill or capsule, subcutaneous, and intravenous. In some implementations, the capsule is formulated to dissolve in a patient's gastrointestinal (GI) tract to reduce or remove undesired metal in the GI tract. In some implementations, the compounds and pharmaceutical compositions provided herein are suitable for topical application, such as in eye drops. In some implementations, the pharmaceutical compositions can be applied directly to the treatment site.

In some implementations compositions comprising the chelating compound further comprise other components to mimic other fluids including, without limitation, synovial fluid, cerebrospinal fluid, aqueous humor, blood (and various blood components including plasma), and lymphatic fluid.

In some implementations, the pharmaceutical compositions contain, in addition to the chelating compound, one or more pharmaceutically acceptable carriers (e.g., excipients). In some implementations, the chelating compound is mixed with an excipient, diluted by an excipient or enclosed within such a carrier in the form of, for example, a capsule, tablet, or other container. When the excipient serves as a diluent, it can be a solid, semi-solid, or liquid material, which acts as a vehicle, carrier or medium for the active ingredient. Thus, the pharmaceutical compositions can be in the form of tablets, pills, powders, suspensions, emulsions, solutions, syrups, aerosols (as a solid or in a liquid medium), soft and hard gelatin capsules, suppositories, sterile injectable solutions, and sterile packaged powders.

Some examples of suitable excipients include, without limitation, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. Pharmaceutical compositions and formulations comprising the pharmaceutical compositions can additionally include, without limitation, lubricating agents such as talc, magnesium stearate, and mineral oil; wetting agents; emulsifying and suspending agents; preserving agents such as methyl- and propylhydroxy-benzoates; sweetening agents; flavoring agents, or combinations thereof.

Methods of Treatment

The present application further provides methods of chelating metal in a patient, comprising administering the chelating compounds provided herein.

As used herein, the term "patient," refers to any animal, including mammals. Example patients include, but are not limited to, mice, rats, rabbits, dogs, cats, swine, cattle, sheep, horses, primates, and humans. In some embodiments, the patient is a human.

The chelating compounds can be used for various applications. For example, applications for both joint spaces and non-joint spaces are possible. More specifically, the chelating compounds can be used in treatments for each of articular joints, non-articular joints, joints with synovium, and joints without synovium. For example, the chelating compound can be used for orthopedic treatments. For example, the chelating compound can be administered into an intra-articular space (e.g., in a hip joint, knee joint, spine, ankle joint, wrist joint, etc.) to remove metal from the intra-articular space. In some examples, the compound can be flushed away or otherwise removed after a period of time period to allow for chelation in patients with metallosis.

The chelating compounds can also be used in applications for non-joint spaces, such as systemic, blood vessels, a heart, a spinal canal, an epidural space, a subcutaneous space, a ventricular space, the uterus, a portion of an alimentary canal, a brain, an intraosseous space, and so forth.

The chelating compound is useful to treat various diseases or disorders. For example, the chelating compound can be used for the treatment of a disease or disorder that is associated with abnormal levels of metal ions and debris in a patient, such as metallosis. In some embodiments, the abnormal amount of metal in the patient refers to about 25% to about 1000% increased concentration of metal in the patient compared to the concentration of metal in a control patient, for example, about 50% to about 1000%, about 25% to about 750%, about 50% to about 750%, about 50% to about 500%, about 50% to about 1000%, about 75% to about 1000%, about 50% to about 500%, about 75% to about 200%, or about 100% to about 1000% increased concentration of metal in the patient compared to the concentration of metal in a control patient.

In some implementations, metallosis can result in a patient following degradation of a metal implant. The metal implant can be an object placed inside the patient that includes metal for at least a portion of the implant. If the metal portion of the implant degrades, excess metal can result in the treatment site including the implant.

In some implementations, the metal implant includes a metal-on-metal (MoM) implant. Similarly, the chelating compounds can be used to prevent diseases or disorders in patients at risk of diseases and disorders associated with abnormal levels of metal including those patients who have a MoM implant but have not been diagnosed as having abnormal levels of metal. For example, the MoM implant can be in an articular joint of the patient, such as a knee, spine, hip, and so forth. A therapeutically effective amount of the chelating compound can be administered to the articular joint of the patient to remove metal present in the joint space of the MoM implant. In some implementations, the metal-on-metal implant is an articular implant selected from the group consisting of a hip implant, a knee implant, a shoulder implant, a wrist implant, a vertebral implant, and an elbow implant.

The metal implant can include a metal-on-polyethylene (MoP) implants. In this case, only a portion of the implant includes metal. However, degradation of the metal portion can still result in adverse effects to the patient (such as metallosis). While MoP implants are generally positioned in joint spaces, the chelating compound can also be used for MoP implants in non-joint spaces.

Similarly, the chelating compound can be used to treat patients having metal implants that are positioned in or near a non-joint space where degradation of the metal implant has occurred (or is expected to occur). The chelating compound can be administered in a therapeutically effective amount to a treatment site (e.g., a non-joint space) of the patient comprising a metal implant in a target site of the patient other than an articular joint (or other joint space). In some implementations, the metal implant can include a stent, mesh, electrodes, biosensors, and so forth.

The chelating compound can be used for treatment of disease or disorders associated with abnormally high levels of metal in the patient. In some implementations, treatment of these diseases or disorders comprises reducing effects of the presence of high levels of metal in the patient. For example, the undesired effects of high levels of metal can be reduced by removing some or all of the excess metal in the patient at a treatment site resulting from degradation of a metal implant. In some implementations, treatment of the diseases or disorders comprises elimination of the effects of high levels of metal in the patient by removing some or all of the excess metal in the patient resulting from degradation of the metal implant.

In some examples the disease or disorder is associated with abnormally high levels of metal in the patient. The chelating compound can be used to reduce the concentration of metal in the patient. In some implementations, the disease or disorder includes one or more of metallosis, allergies (including metal hypersensitivity), heavy metal poisoning, hard metal pneumoconiosis (occupational exposure), vineyard sprayers lung (occupational exposure), soft tissue inflammatory reactions, chronic inflammation, pseudotumors, aseptic lymphocytic vasculitis associated-lesion (ALVAL), bursae, adverse reactions to metal debris (ARMD), implant loosening, osteolysis, and metabolic conditions associated with undesired levels of metals (including Wilson's disease, haemosiderosis, and haemochromatosis).

Various administration methodologies are possible. In some implementations the chelating compound is administered parenterally. The chelating compound can also be administered directly to a joint space or a non-joint space localized at the metal implant in the patient. For example, the chelating compound can be administered by an injection at the treatment site. In some implementations, the treatment site can include a joint (e.g. articular joint, synovial joint), a blood vessel, a heart, a spinal canal, a subcutaneous space, an epidural space, a ventricular space, a uterus, a portion of an alimentary canal, and an intraosseous space, though other similar sites are possible.

In an aspect, following one or more administrations of the chelating compound to the treatment site, the treatment site can then be flushed at least once with a wash solution comprising hyaluronic acid dissolved in saline. In some implementations, the chelating compound is left at the treatment site.

The chelating compound can be effective over a wide dosage range and are generally administered in a pharmaceutically effective amount. It will be understood, however, that the amount of the chelating compound actually administered will usually be determined by a physician, according to the relevant circumstances, including the condition to be treated, the chosen route of administration, the actual compound administered, the age, weight, and response of the individual subject, the severity of the subject's symptoms, and the like.

The chelating compound also finds use in treating diseases or disorders (e.g. metallosis) in patients with metal implants by administering an effective amount of the chelating compound to a patient, the method comprising: (a) applying the chelating compound comprising a glycosaminoglycan moiety and one or more chelating agent to an area of treatment of the patient; and (b) chelating metals to remove the metal from the area of treatment. Other applications of the chelating compound include, without limitation, use of a chelating compound comprising a glycosaminoglycan moiety and one or more chelating agent for use in treating diseases and disorders (e.g. metallosis) in patients with a metal implant, wherein applying the chelating compound to an area of treatment of the patient chelates metal, thereby removing the metal ions from the area of treatment.

EXAMPLES

Characterization of BAL Functionalized Hyaluronic Acid (BAL-HA)

Figure 2A:
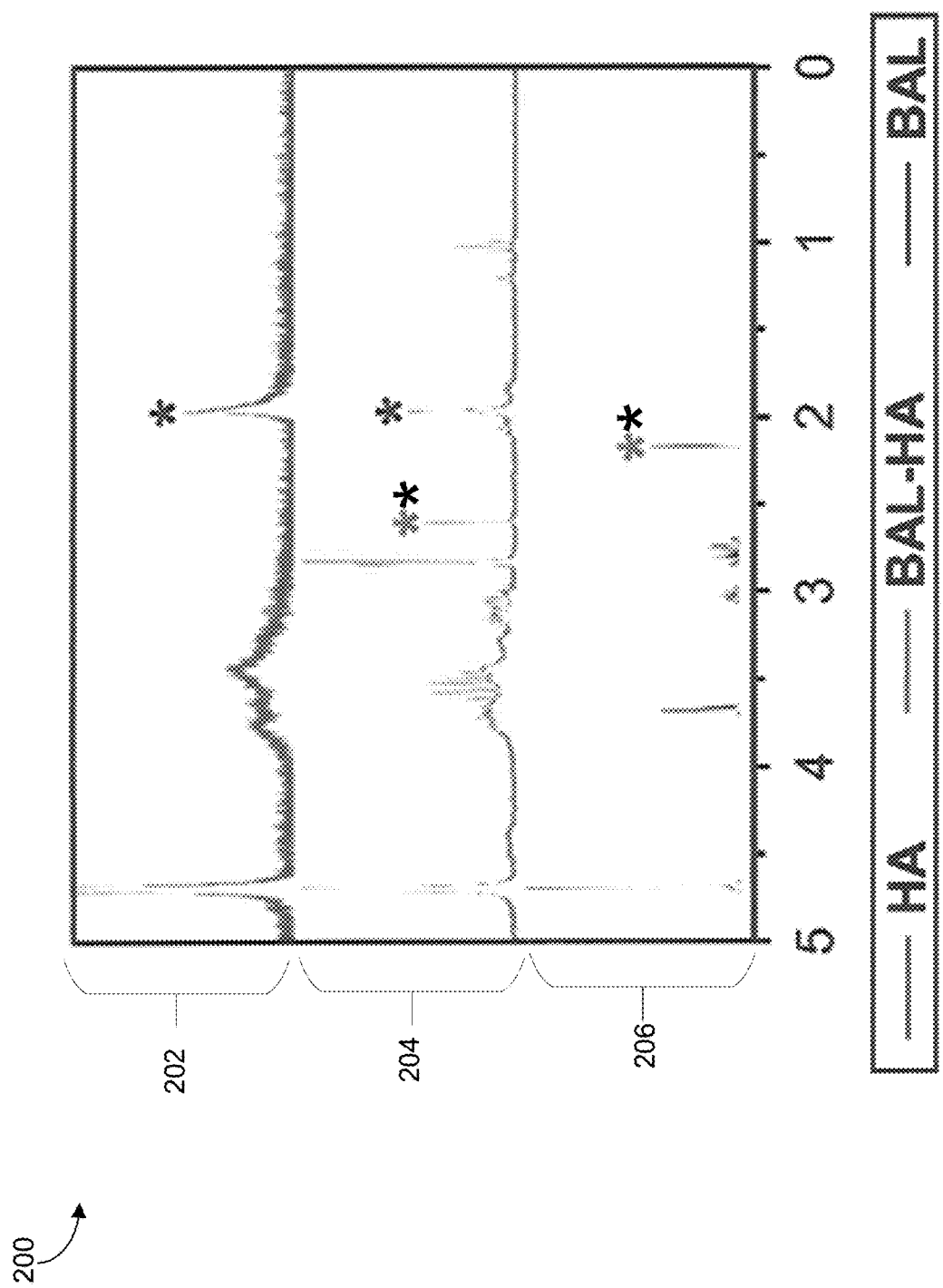
FIGS. 2A-2C show data representing characterizations of the chelating compound including hyaluronic acid.
Figure 2B:
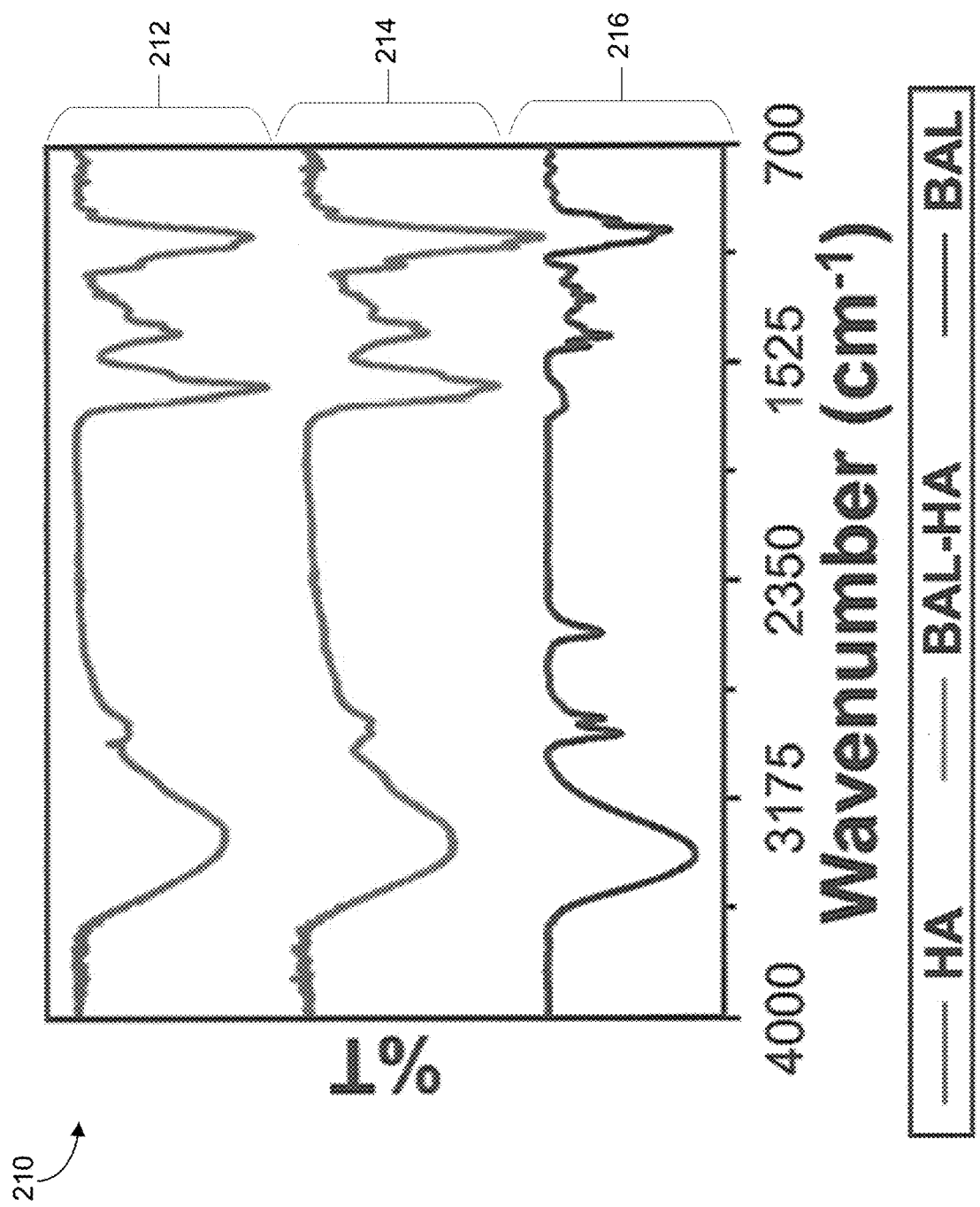
Figure 2C:
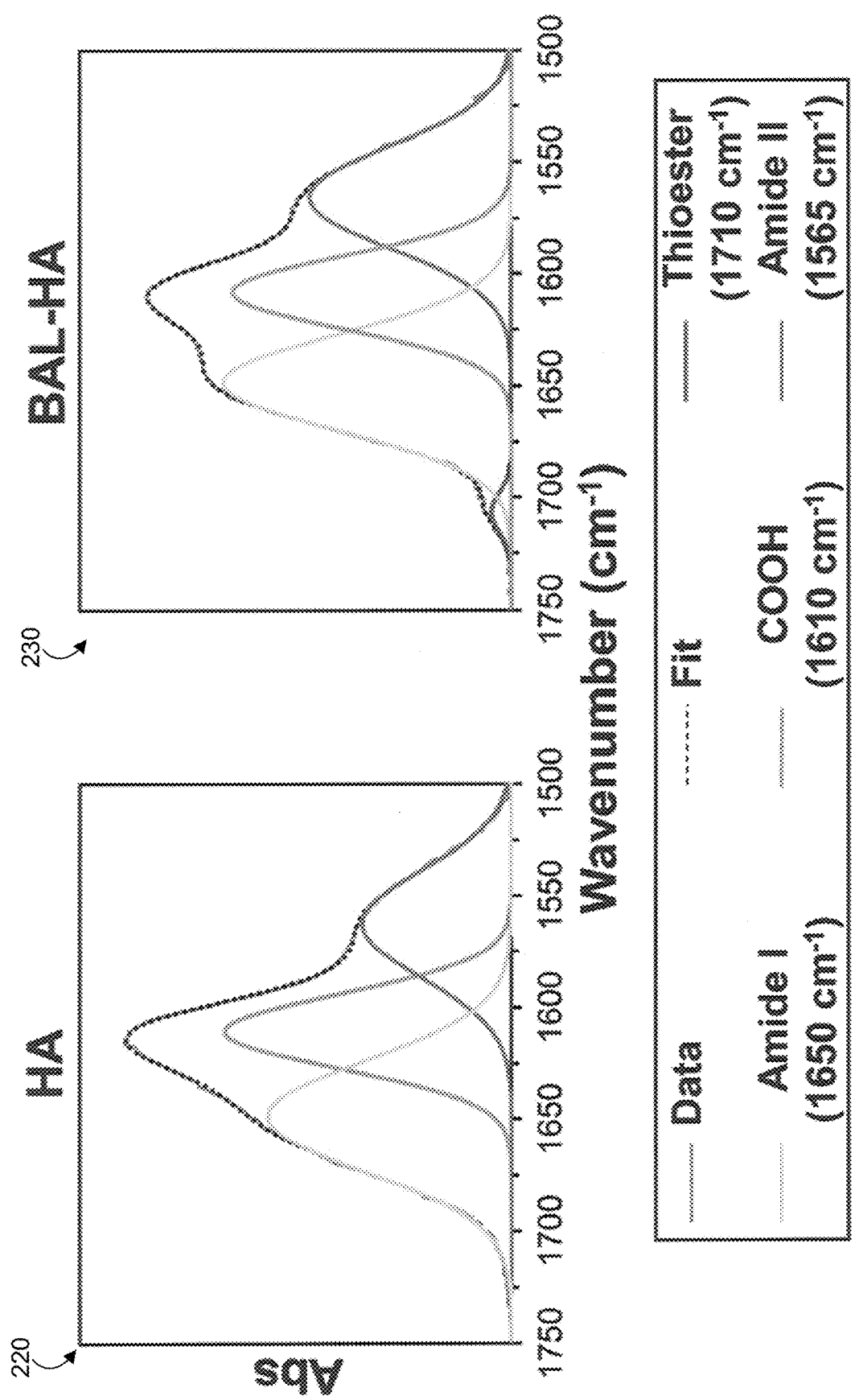

Turning to FIGS. 2A-2C, a characterization of the chelating compound confirmed successful covalent coupling of BAL to HA. For example, as shown in graph 200 of FIG. 2A, $^1$H NMR of BAL-HA displays the emergence of chemical shifts associated with BAL. However, chemical shifts unique to BAL overlap with HA, making interpretation of the structure of the covalent coupling difficult. Peak deconvolution of FTIR spectra in the carbonyl region (1750-1500 $cm^{-1}$), shown in graphs 220 and 230 of FIG. 2C, indicate the emergence of a thioester peak at 1710 $cm^{-1}$ for BAL-HA while the carboxylic acid peak at 1610 $cm^{-1}$ remained constant. Thus, thiol functional groups, rather than the primary alcohol, on BAL were responsible for covalent coupling to HA. Since primary thiols are stronger nucleophiles than secondary thiols, we conclude that the primary thiol serves as the main nucleophilic moiety for chemical modification.

Graph 200 of FIG. 2A shows $^1$H NMR in D$_2$O, where* denotes N-acetyl protons on the HA backbone and ** denotes thiol proton shifts from BAL. Graph 210 of FIG. 2B shows FTIR spectra for HA 212, BAL-HA 214, and BAL 216 from 4000-700 cm$^{-1}$ in percent transmittance. Graphs 220 and 230 of FIG. 2C show de-convoluted FTIR spectra from 1750-1500 cm$^{-1}$ in absorbance.

After chemical modification, qualitative observations revealed a decrease in the solubility of BAL-HA, likely due to the modification of free carboxylic acid groups into less ionizable functional groups. Dynamic Light Scattering (DLS) and zeta potential measurements were used to further evaluate this observation, providing insight into the effects of BAL modification on polymer flocculation and electrostatic charge, respectively. DLS particle size measurements show BAL-HA has substantially larger particle sizes than the HA starting material. Zeta potential measurements reveal BAL-HA has a lower electrostatic charge than unmodified HA due to the incorporation of BAL molecules that contain less ionizable moieties. Modification of large polymers with small molecule chelating agents, such as BAL, will have minimal effect on particle size. Therefore, the increase in particle size for BAL-HA materials is due to decreased water solubility resulting in flocculation.

Figure 3A:
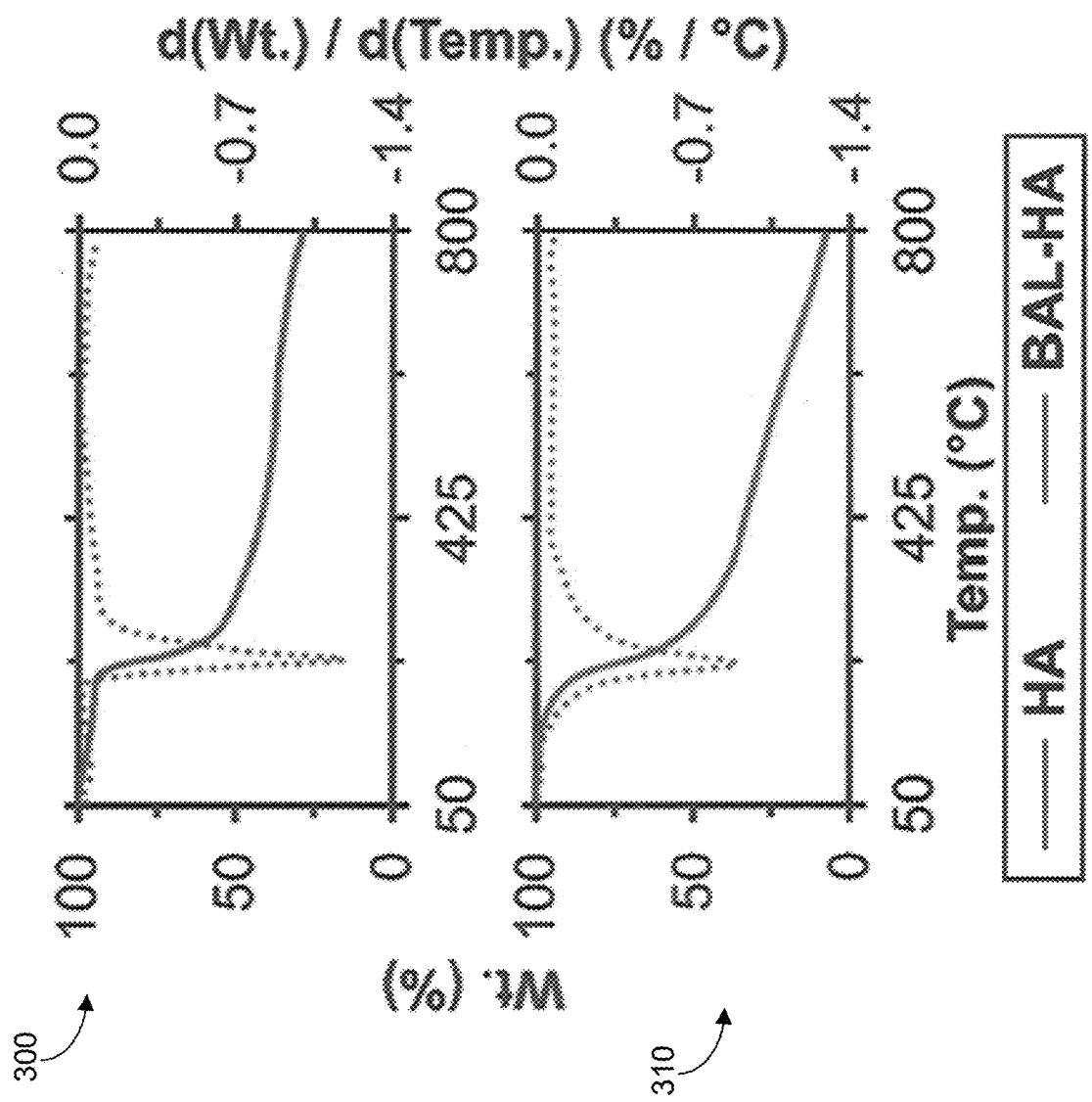
FIGS. 3A-3B show data representing quantification of a functionalization efficiency of the chelating compound.
Figure 3B:
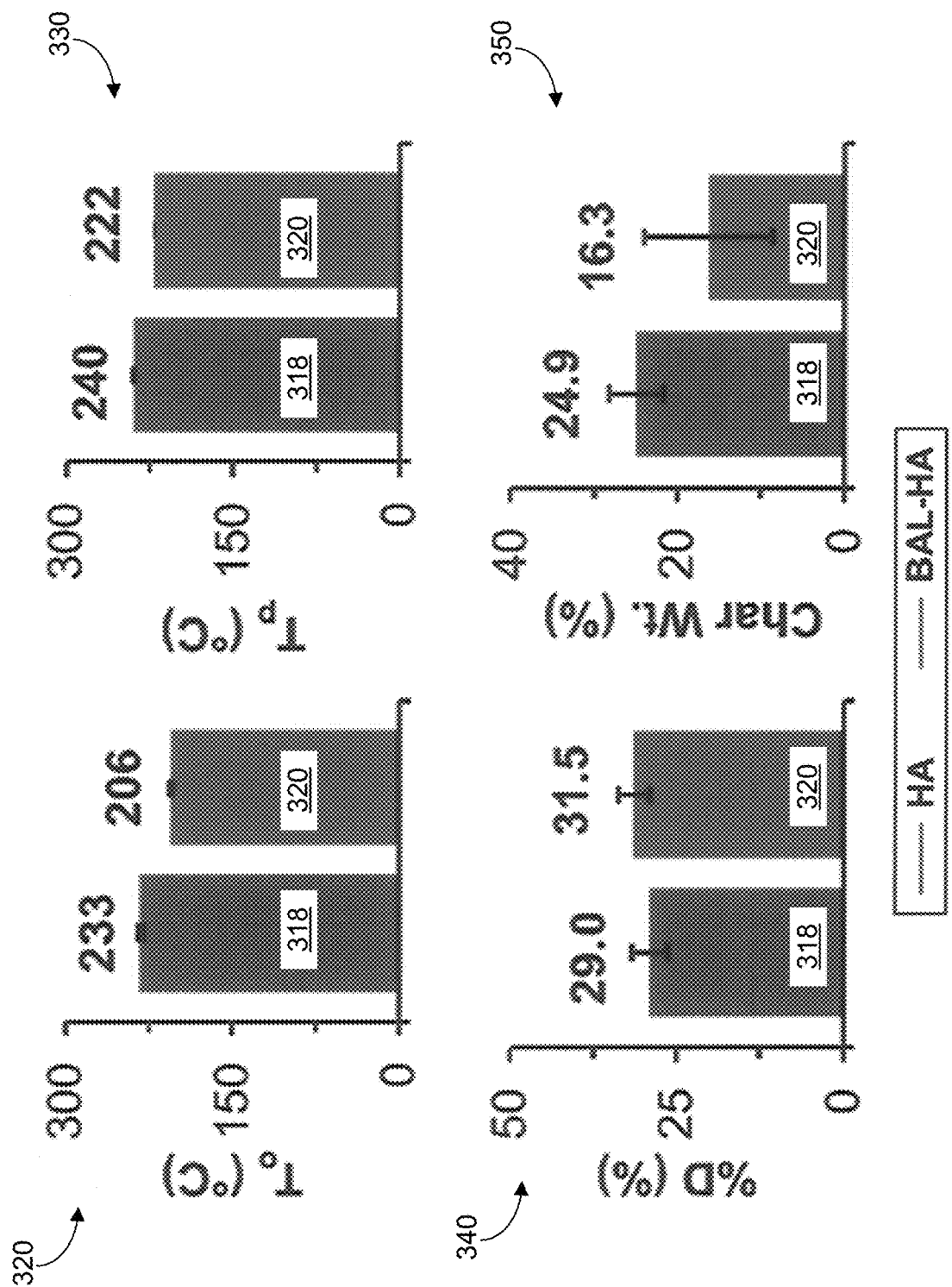

The functionalization efficiency (FE) of the coupling scheme to the polymeric backbone of the chelating compound was evaluated because the coupling scheme directly affects the capacity for metal chelation. Turning to FIGS. 3A-3B, TGA was used to quantify FE. HA and BAL-HA thermogravimetric (TGA) thermograms (graphs 300 and 310, respectively) display one degradation event. The BAL-HA degradation event broadens with a shift to a lower onset temperature (To); a lower first derivative peak temperature ($T_p$); a higher weight loss of the primary degradation event (% D); and a lower char weight, all of which indicate the evolution of additional mass from BAL. However, the difference in the weight loss of the primary degradation event between BAL-HA and HA is indicative of the weight percent of BAL on the polymer backbone. Using the weight percent of conjugated BAL, the FE was calculated to be 9.8±1.3% as shown using the following equations (1) and (2).

$$FE\bar{x} = (\% D_{BAL-HA} - \% D_{HA})\left(\frac{1 \text{ mol } BAL-HA}{1 \text{ mol } BAL}\right)\left(\frac{487.535 \text{ g } BAL-HA}{124.216 \text{ g } BAL}\right) \quad (1)$$

$$FE\sigma_x = \sqrt{\sigma_{HA}^2 + \sigma_{BAL-HA}^2} \quad (2)$$

BAL-HA was also evaluated using the Ellman's assay and the BAL FE was 10.7±2.9%.

In graphs 300 and 310 of FIG. 3A, TGA of HA and BAL-HA are shown. The thermograms (solid lines) and the first derivative of the thermograms (dashed lines) are included. FIG. 3B shows graphs 320, 330, 340, and 350 that include a quantification of the TGA data. Graph 320 shows To which includes the onset temperature of the degradation event. Graph 330 shows $T_p$ which is the first derivative peak temperature calculated from the local minima of the first derivative of the degradation curve. Graph 340 shows the weight loss percentage for the degradation event at $T_o$. Graph 350 shows the char weight percent is the weight percent remaining at 800° C. The error bars are the sample standard deviation from triplicate runs of HA and three different batches of BAL-HA.

The BAL FE was used to calculate the amount of cobalt, nickel, and chromium that 1 mg of BAL-HA could theoretically chelate in a 1:1 monomer:metal ion ratio, shown in Equations (3) and (4). The results are presented in Table 1.

$$\text{Theorectical } \bar{x} \, M^{x+} \text{ Chelation} = \quad (3)$$
$$\left(\frac{FE}{1 \text{ mg } BAL-HA}\right)\left(\frac{1 \text{ g}}{1000 \text{ mg}}\right)\left(\frac{1 \text{ mol}}{487.535 \text{ g } BAL-HA}\right)$$
$$\left(\frac{1 \text{ mol } M^{x+}}{1 \text{ mol } BAL-HA}\right)\left(\frac{g \, M^{x+}}{1 \text{ mol } M^{x+}}\right)\left(\frac{1 \times 10^6 \, \mu g}{1 \text{ g}}\right)$$

$$\text{Theorectical } \sigma_x \, M^{x+} \text{ Chelation} = \quad (4)$$
$$\left(\frac{\sigma_x \, FE}{1 \text{ mg } BAL-HA}\right)\left(\frac{1 \text{ g}}{1000 \text{ mg}}\right)\left(\frac{1 \text{ mol}}{487.535 \text{ g } BAL-HA}\right)$$
$$\left(\frac{1 \text{ mol } M^{x+}}{1 \text{ mol } BAL-HA}\right)\left(\frac{g \, M^{x+}}{1 \text{ mol } M^{x+}}\right)\left(\frac{1 \times 10^6 \, \mu g}{1 \text{ g}}\right)$$

|  | Cobalt (μg) | Nickel (μg) | Chromium (μg) |
| --- | --- | --- | --- |
| TGA | 11.8 ± 1.6 | 11.8 ± 1.6 | 10.5 ± 1.4 |
| Ellman's assay | 12.9 ± 3.3 | 12.9 ± 3.3 | 11.4 ± 2.9 |

Based on clinical case studies, maximum amounts of cobalt, nickel, or chromium in synovial fluid surrounding metal prostheses are 259, 388, and 1470 μg, respectively. Considering this, the chelation ability of the polymeric system demonstrates therapeutic relevance to patients suffering metallosis due to metal implant failures.

Qualitative Chelation Capacity of BAL-HA

The chemical modification scheme for the chelating compound 104 successfully incorporated BAL onto the backbone of HA. The efficacy of the polymeric system to chelate transition metals was evaluated. BAL, which is a clear liquid, forms strongly colored chelating complexes with cobalt and nickel ions.

This colorimetric response results from the formation of cobalt or nickel-BAL coordination complexes. Thus, colorimetry can be used as an indicator of chelation. Considering this, dispersions of BAL-HA in water were spiked with dilute concentrations of $Co^{2+}$, $Ni^{2+}$, $Cr^{3+}$, and $Cr^{6+}$. Cobalt and nickel solutions displayed a significant color change upon contact with BAL-HA, a phenomenon not observed with the unmodified HA control. Thus, colorimetry can be successful utilized for BAL-HA chelation of cobalt and nickel, proving BAL retains the ability to chelate transition metals even after conjugation to the polymeric scaffold.

Chromium chelation did produce a visible colorimetric response to either bare BAL or BAL-HA, though BAL is known to chelate chromium. With the success of cobalt and nickel chelation, it can be seen that the polymeric system retains the capacity to chelate transition metals and can be extended to chromium chelation. Hard Soft Acid Base (HSAB) theory shows that primary alcohols serve as the primary moieties for chromium chelation due to the hard-hard interaction. HA already contains primary alcohols on the polymeric backbone that could participate in chelation. Chelation could further be enhanced since BAL conjugation to the HA is primarily facilitated by primary thiols, leaving additional alcohol moieties free for chromium coordination.

To qualitatively evaluate the strength of the chelation, the solutions were dialyzed against water to remove excess metal from the samples. Even after several days of dialysis, BAL-HA retained cobalt and nickel ions as indicated by the color of the samples. After freeze drying, BAL-HA spiked with cobalt and nickel remained dark brown.

Quantitative BAL-HA Cobalt Chelation

Figure 4A:
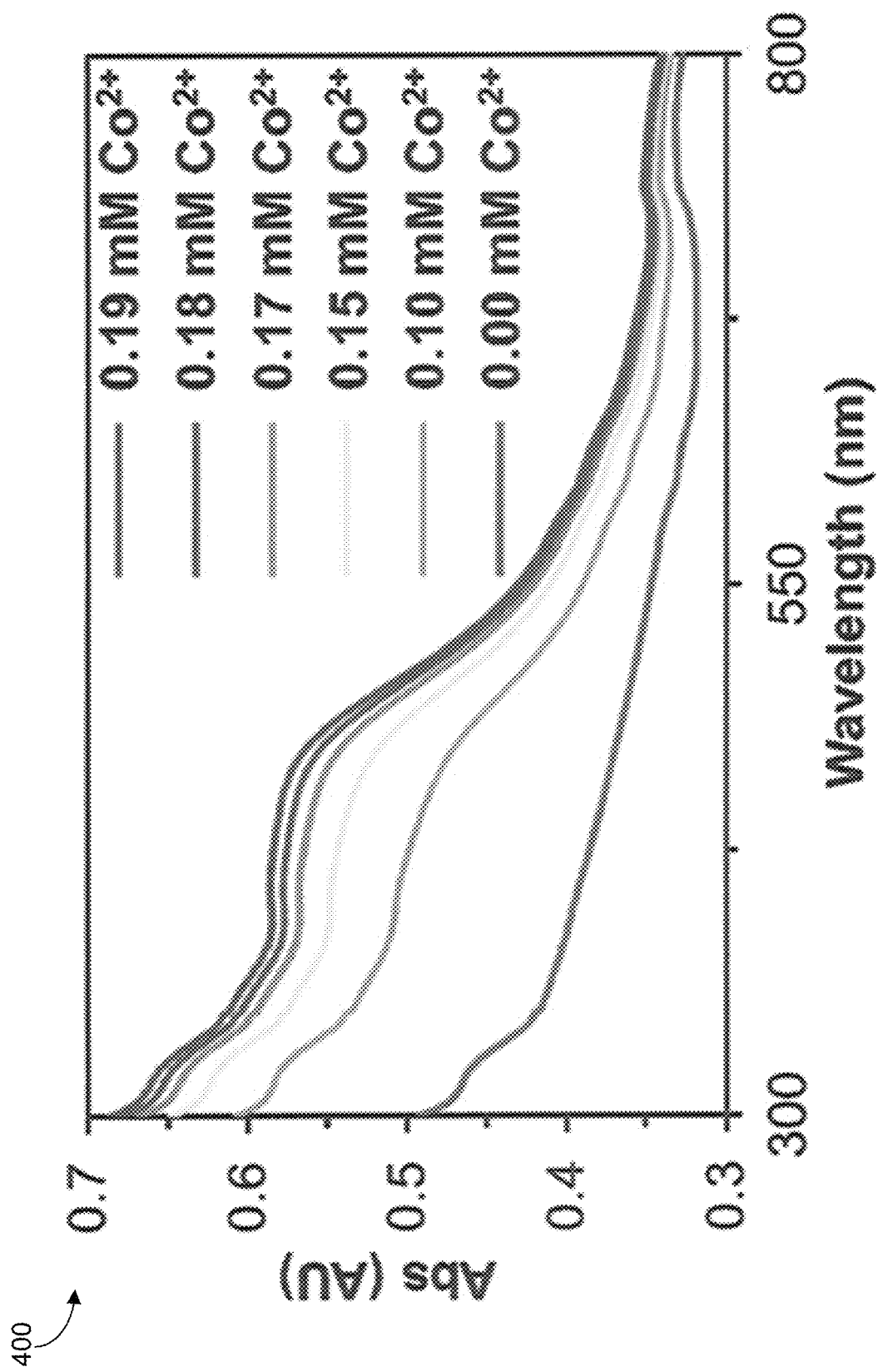
FIGS. 4A-4D show data representing absorbance titration of BAL-HA with $Co^{2+}$.

Absorption titrations with cobalt were used as a quantitative approach for BAL determination. Graph 400 of FIG. 4A shows data resulting from quantitatively exploring BAL-HA cobalt chelation. UV-visible absorbance spectra show the emergence of a peak at 475 nm as cobalt is added to BAL-HA that plateaus in absorbance after the endpoint is reached and the polymer is saturated. Deconvolution of the absorbance spectra from 430-530 nm before the endpoint is reached display two peaks at 455 and 475 nm corresponding to spin-orbit effects and chelated cobalt, respectively. After the endpoint is reached, a peak at 500 nm emerges that corresponds to free cobalt.

Figure 4B:
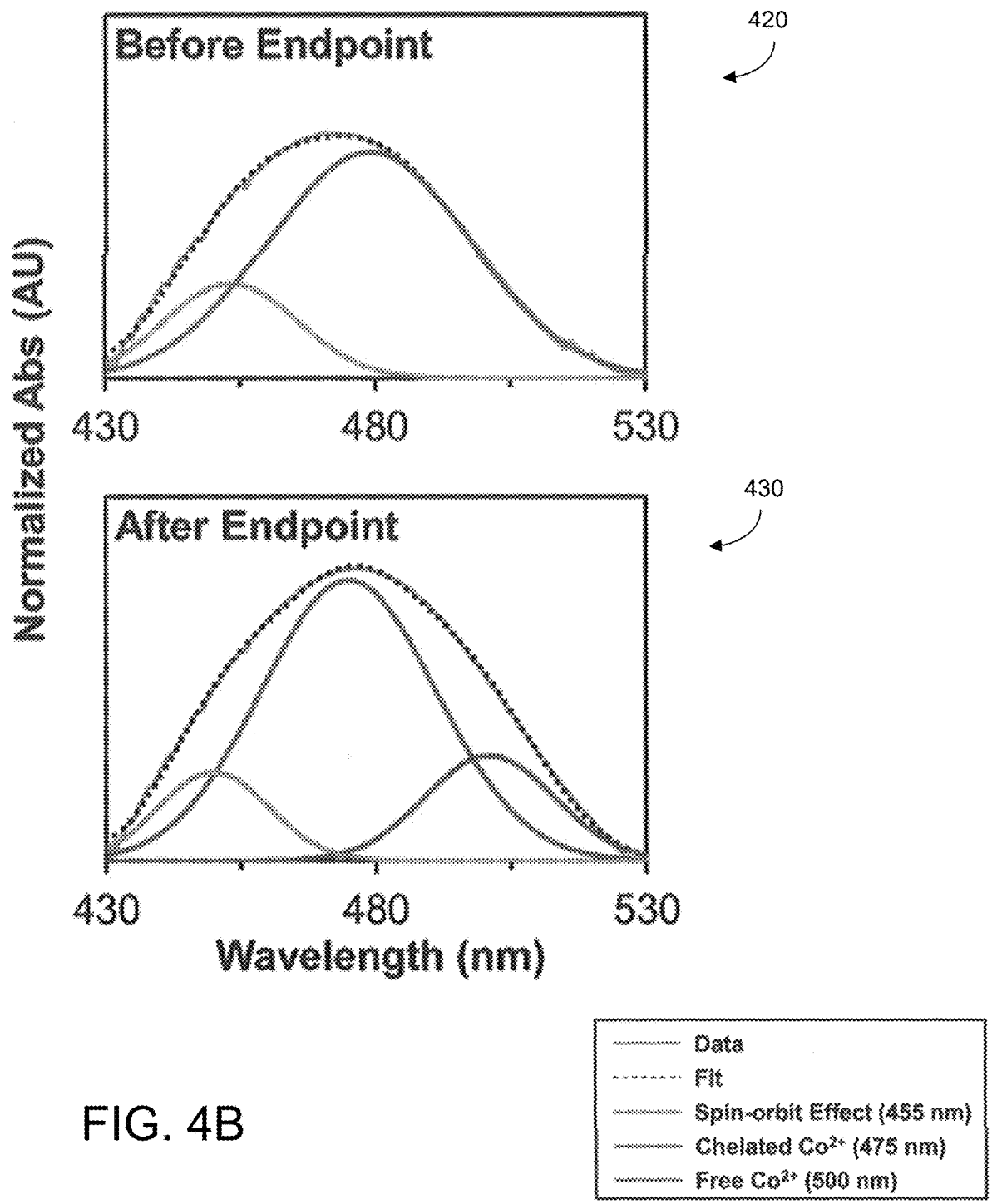
Figure 4C:
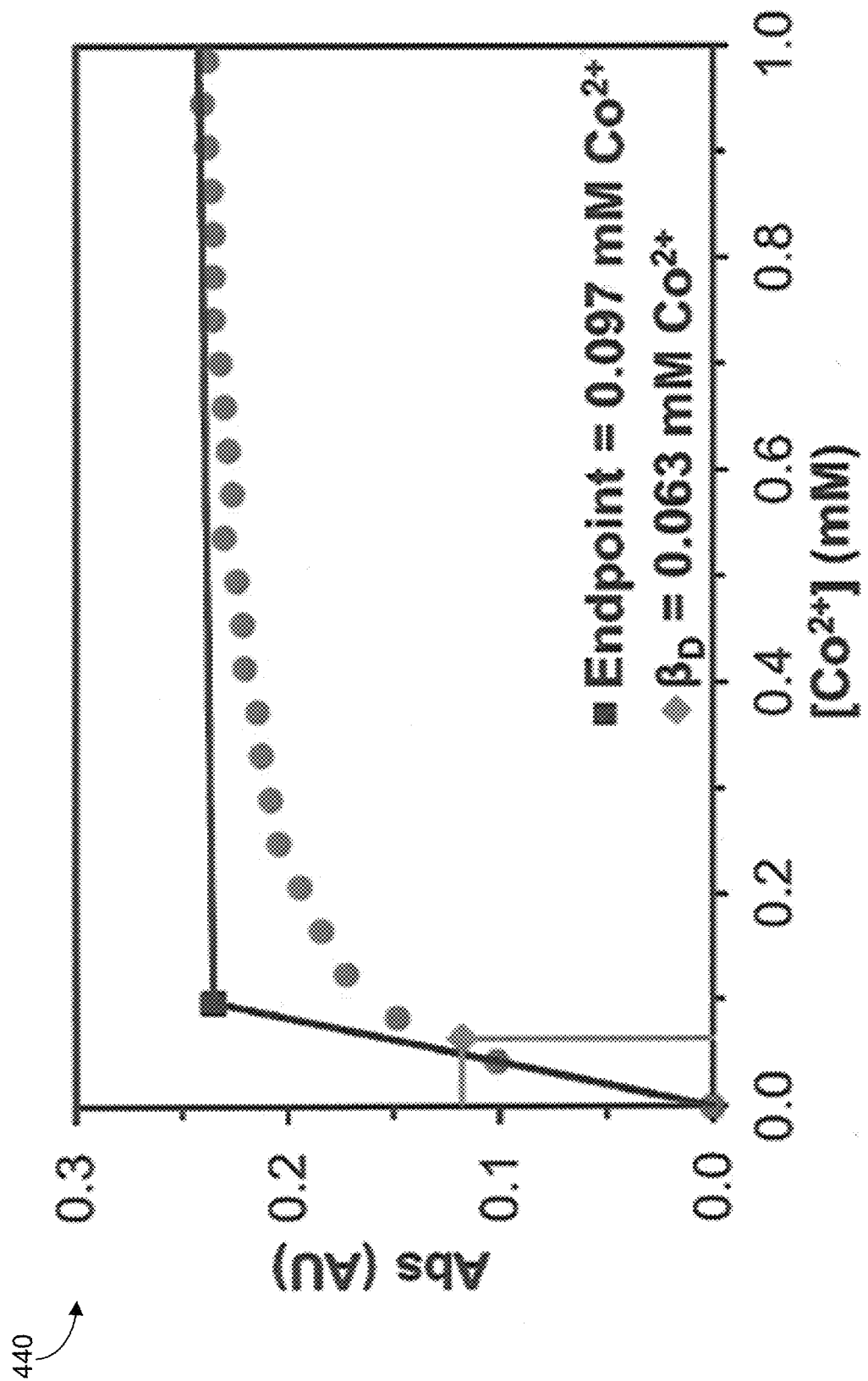
Figure 4D:
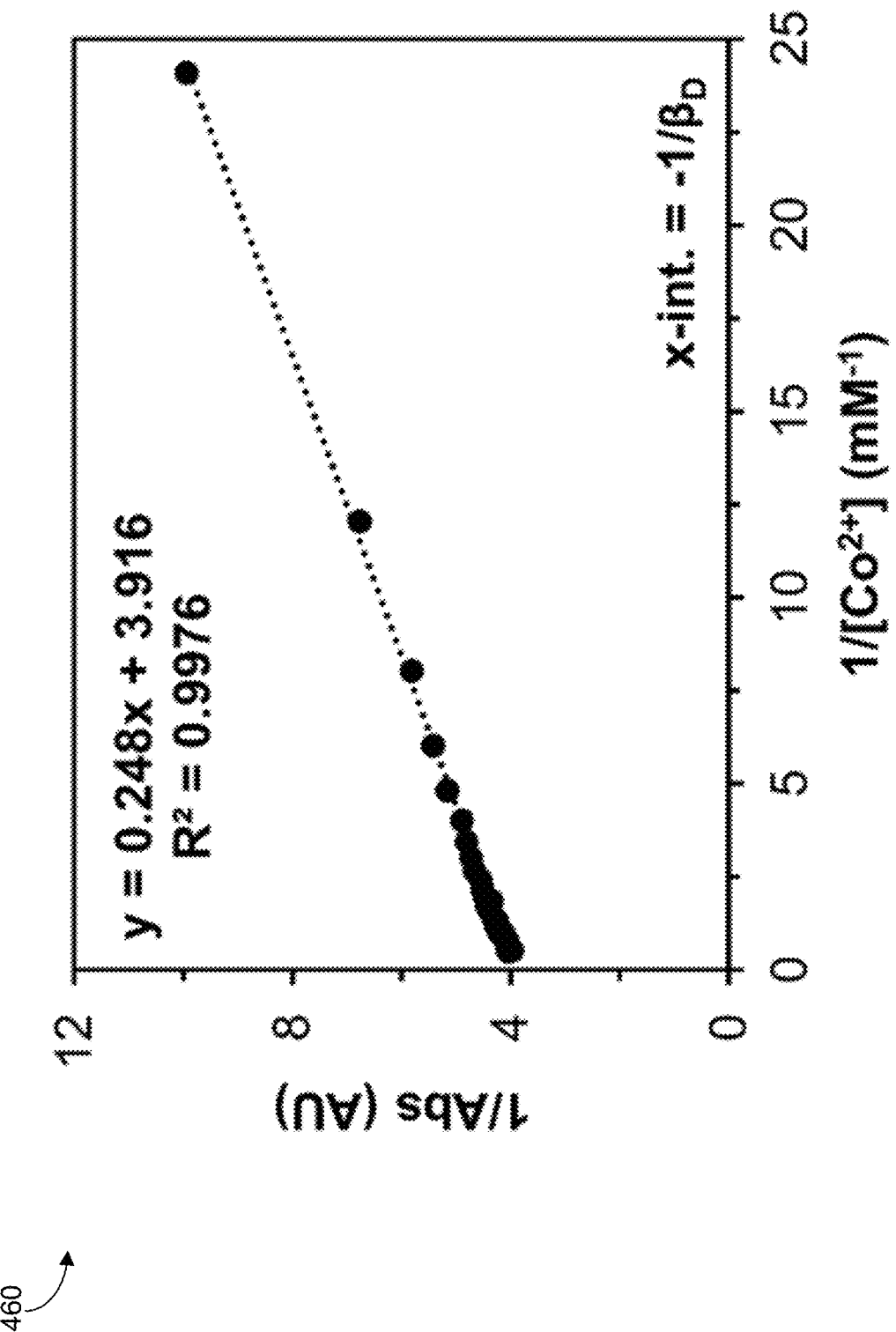

FIGS. 4A-4D show absorbance titration of BAL-HA with $Co^{2+}$. Graph 400 of FIG. 4A shows UV-visible spectral overlay of BAL-HA from 300-800 nm as a function of cobalt addition. Graphs 420 and 430 of FIG. 4B shows peak deconvolution of absorbance spectra from 430-530 nm before and after the endpoint of the titration was reached. Graph 440 of FIG. 4C shows absorbance titration curve at 475 nm with the endpoint and overall dissociation constant Wo displayed. Absorbances were baseline corrected against BAL-HA and cobalt concentration corrected for dilution effects.

An absorbance titration curve was generated using absorbance values at 475 nm as a function of cobalt added, generating an inverted L-shaped curve. The endpoint was determined by extrapolation of two straight lines and used to calculate the mass of cobalt chelated per mg of BAL-HA, as shown in Equation (5).

$$\text{Experimetnal Mass of Chelated Co}^{2+} = \left(\frac{[Co^{2+}] \text{ at Endpoint}}{\text{Mass of } BAL-HA}\right) \tag{5}$$

$$\left(\frac{\text{Total Volume}}{1000 \text{ mM}}\right)\left(\frac{58.933 \text{ g Co}^{2+}}{1 \text{ mol}}\right)\left(\frac{1 \times 10^6 \text{ }\mu g}{1 \text{ g}}\right)$$

The experimental mass of cobalt chelated per mg of BAL-HA was 5.7 μg, which is less than the theoretical amount calculated by TGA and the Ellman's assay in Table 1. However, the experimental mass of chelated cobalt is approximately half of the theoretical mass. This strongly indicates that the monomer:cobalt ion chelation ratio is 2:1 rather than 1:1, which has been reported with bare BAL.

Further, quantitative analysis of cobalt chelation allows calculation of the approximate amount of BAL-HA required for in vivo metal chelation in joint cavities. HA injections are used as a therapy for osteoarthritis, with therapeutic parameters for several hip injections shown in Table 2.

TABLE 2

FDA Approved Hyaluronic Acid Hip Injections for Osteoarthritis

| Brand Name | Molecular Weight (kDa) | Concentration of Injection (mg mL$^{-1}$) | Injection Volume (mL) | Number of Dosages |
|---|---|---|---|---|
| Hyalgan ® | 500-730 | 10 | 2.0 | 5 |
| Orthovisc ® | 1000-2900 | 15 | 2.0 | 3-4 |
| Supartz ® | 620-1170 | 10 | 2.5 | 5 |

Using these approved therapeutic parameters as a model, the mass, concentration, injection volume, and number of injections with BAL-HA required to completely chelate cobalt in vivo in severe cobalt metallosis cases can be determined, as shown in Equation (6) and Table 3, below.

$$\left(\frac{\text{Experimental mg } BAL - HA}{\text{Experimental } \mu g \text{ of } M^{x+}}\right) = \tag{6}$$

$$\left(\frac{\text{Theorectical mg } BAL - HA}{\text{Maximum } \mu g \text{ } M^{x+} \text{ in Synovial Fluid}}\right)$$

Assuming the efficiency of BAL-HA chelation of nickel and chromium mirrors that of cobalt, therapeutic parameters can also be determined for severe nickel and chromium metallosis. However, it must be noted that chromium chelation with BAL-HA may be grossly underestimated due to the contributions of alcohol moieties on the HA backbone, as discussed previously.

TABLE 3

Theoretical Therapeutic Parameters of BAL-HA Injections for Total Chelation of Cobalt, Nickel, and Chromium from Hip Joint Fluid

| | Mass of Metal in Synovial Fluid (μg) | BAL-HA (mg) | Concentration of Injection (mg/mL) | Injection Volume (mL) | Number of Injections |
|---|---|---|---|---|---|
| Cobalt | 259 | 45.4 | 15 | 3.0 | 1 |
| Nickel* | 388 | 68.1 | | 4.5 | |
| Chromium* | 1,470 | 258 | | 17 | |

*Denotes theoretical values based on quantification of cobalt chelation.

Quantitative information on the strength of BAL-HA cobalt chelation was also determined using the absorbance titration. The titration data was linearized into a modified Lineweaver-Burk plot, shown in graph 460 of FIG. 4D to extrapolate the overall dissociation constant ($\beta_3 D$), which was 63.3 μM. This enabled calculation of the overall association constant ($\beta_A$), which is the inverse of $\beta_3 D$, and the stability constant ($\log_{10}(\beta_A)$) of chelation. The large values of $\beta_A$ and ($\log_{10}(\beta_A)$), which were $1.58 \times 10^3$ M$^{-1}$ and 4.2, respectively, indicate stable coordination between BAL-HA and cobalt. Further, the Gibbs free energy of binding (G-binding) for cobalt chelation was calculated to be −8.5 kJ, as determined using Equation (7).

$$\Delta G_{binding} = -RT \ln(\beta_A*[BAL-HA]) \tag{7}$$

The large, negative value of cobalt coordination with BAL-HA shows chelation is spontaneous and favorable.

BAL-CS

Figure 5A:
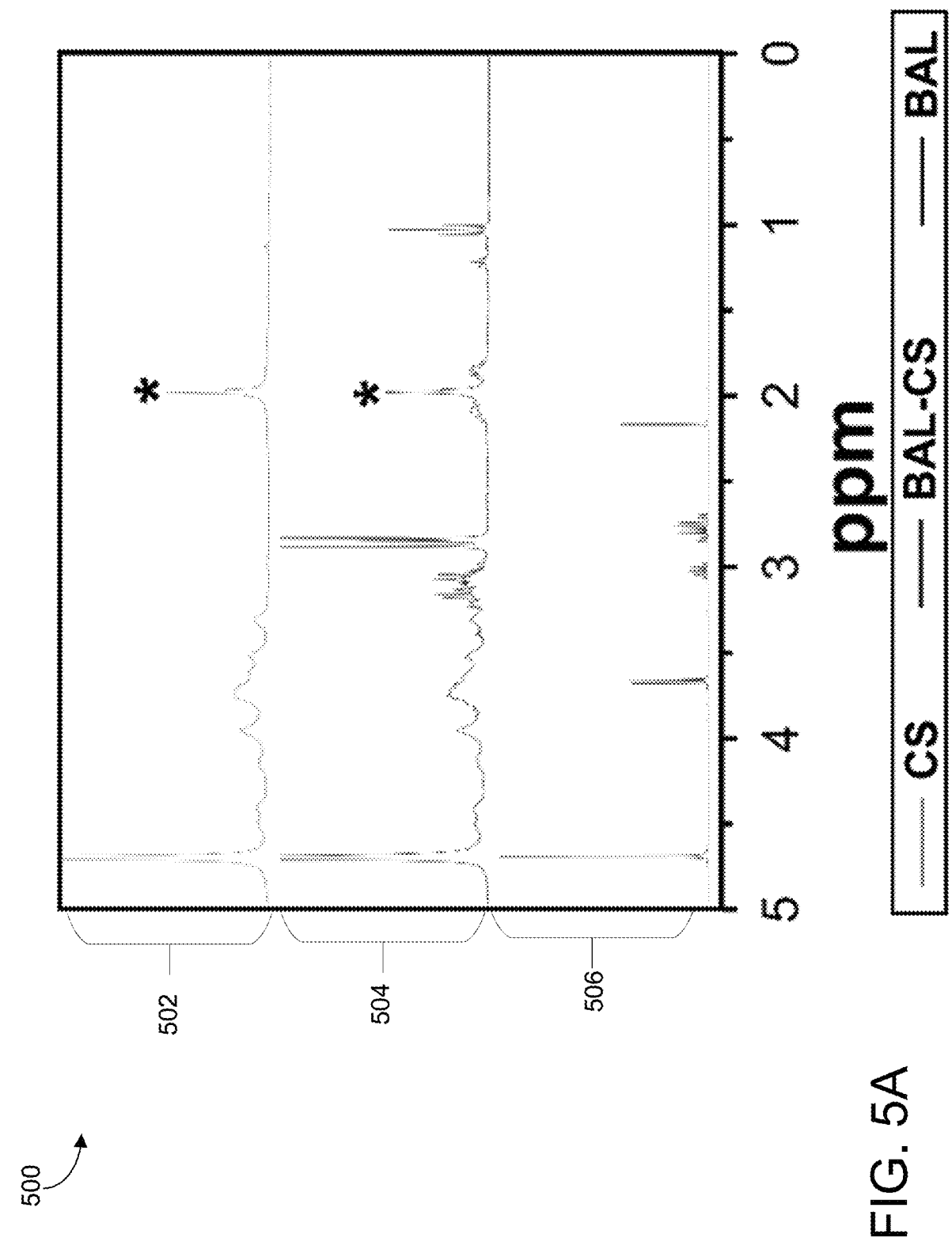
FIGS. 5A-5C show data representing characterizations of the chelating compound including chondroitin sulfate.
Figure 5B:
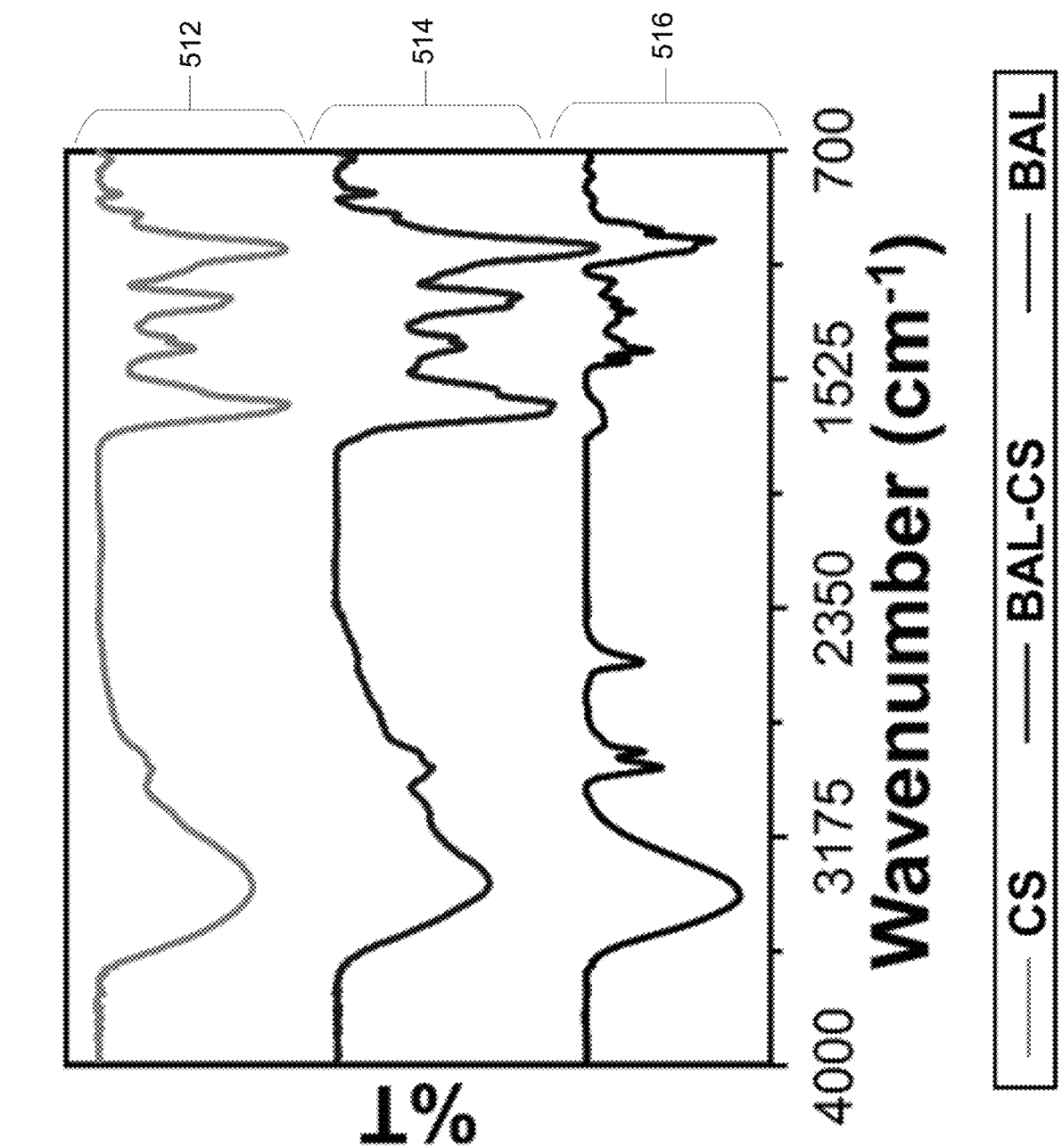
Figure 5C:
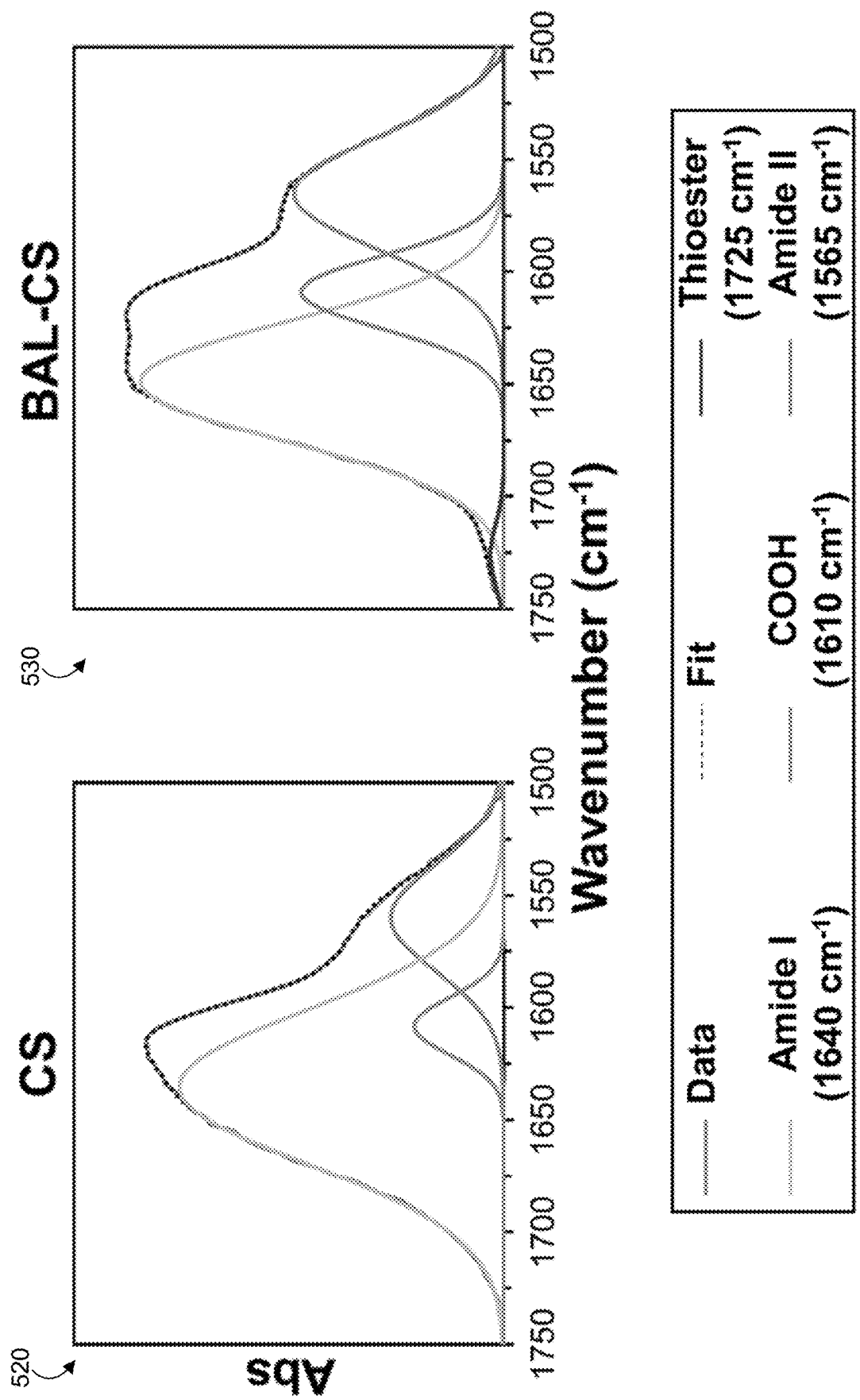
Figure 6A:
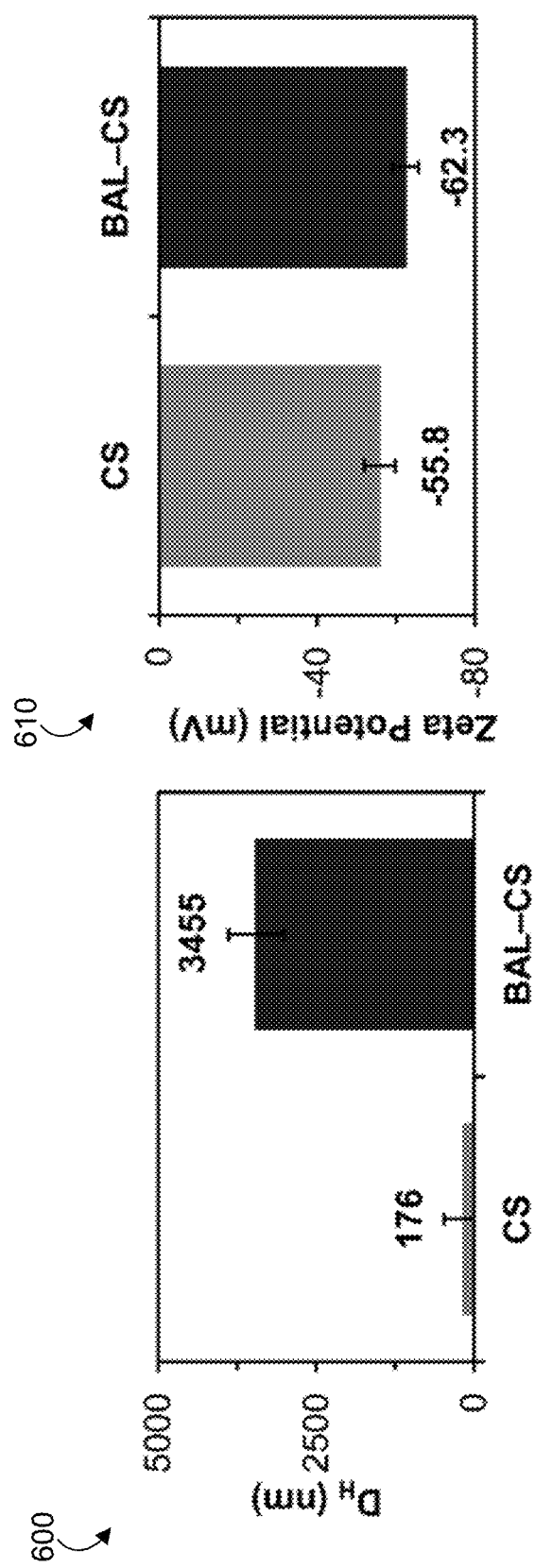
FIGS. 6A-6C show data representing quantification of a functionalization efficiency of the chelating compound.

BAL coupling chemistry was extended to other GAGs, focusing on CS due to its excellent water solubility. FIGS. 5A-5C show data representing characterizations of the chelating compound including CS. Characterization of BAL-CS demonstrated successful BAL functionalization due to the emergence of chemical shifts unique to BAL in the proton NMR spectra of the modified polymer. FTIR peak deconvolution also displayed the emergence of a thioester peak at 1725 cm$^{-1}$, indicating that BAL coupling to the polymer backbone was initiated via the primary thiol on BAL FIG. 5A shows graph 500 which represents 1H NMR in D2O, where * denotes N-acetyl protons on the CS backbone (FIG. S6). Trace 502 represents CS, trace 504 represents BAL-CS, and trace 506 represents BAL. FIG. 5B includes graph 510 representing FTIR spectra from 4000-700 cm-1 in percent transmittance. Trace 512 represents CS, trace 514 represents BAL-CS, and trace 516 represents BAL. FIG. 5C shows graphs 520 and 530, which represent deconvoluted FTIR spectra from 1750-1500 cm-1 in absorbance. Much like BAL-HA, a reduction in solubility was observed after BAL coupling to the CS backbone. DLS and zeta potential measurements showed an increase in particle size, resulting from flocculation, and a reduction in electrostatic charge for BAL-CS FIG. 6A shows particle size and Zeta potential analysis HA and BAL-HA in DI water (1 mg mL-1). Graph 600 shows DLS determined hydrodynamic diameter (DH). Graph 610 shows data representing the corresponding zeta potentials for CS and BAL-CS.

The BAL FE was determined via TGA and the Ellman's assay, which were 25.7±9.8% and 7.28±0.11%, respectively. BAL-CS had a less intense colorimetric response when exposed to cobalt and nickel ions (FIG. S10) during the qualitative chelation study. After dialysis against DI water, BAL-CS samples spiked with cobalt retained a brownish color but nickel was not retained. This indicated that BAL-CS did not chelate as strongly as BAL-HA; however, BAL-CS could prove advantageous as a standalone therapy or a composite with BAL-HA due to its excellent water solubility, enabling easier in vivo delivery of the chelating polymer system into joint cavities.

Figure 6B:
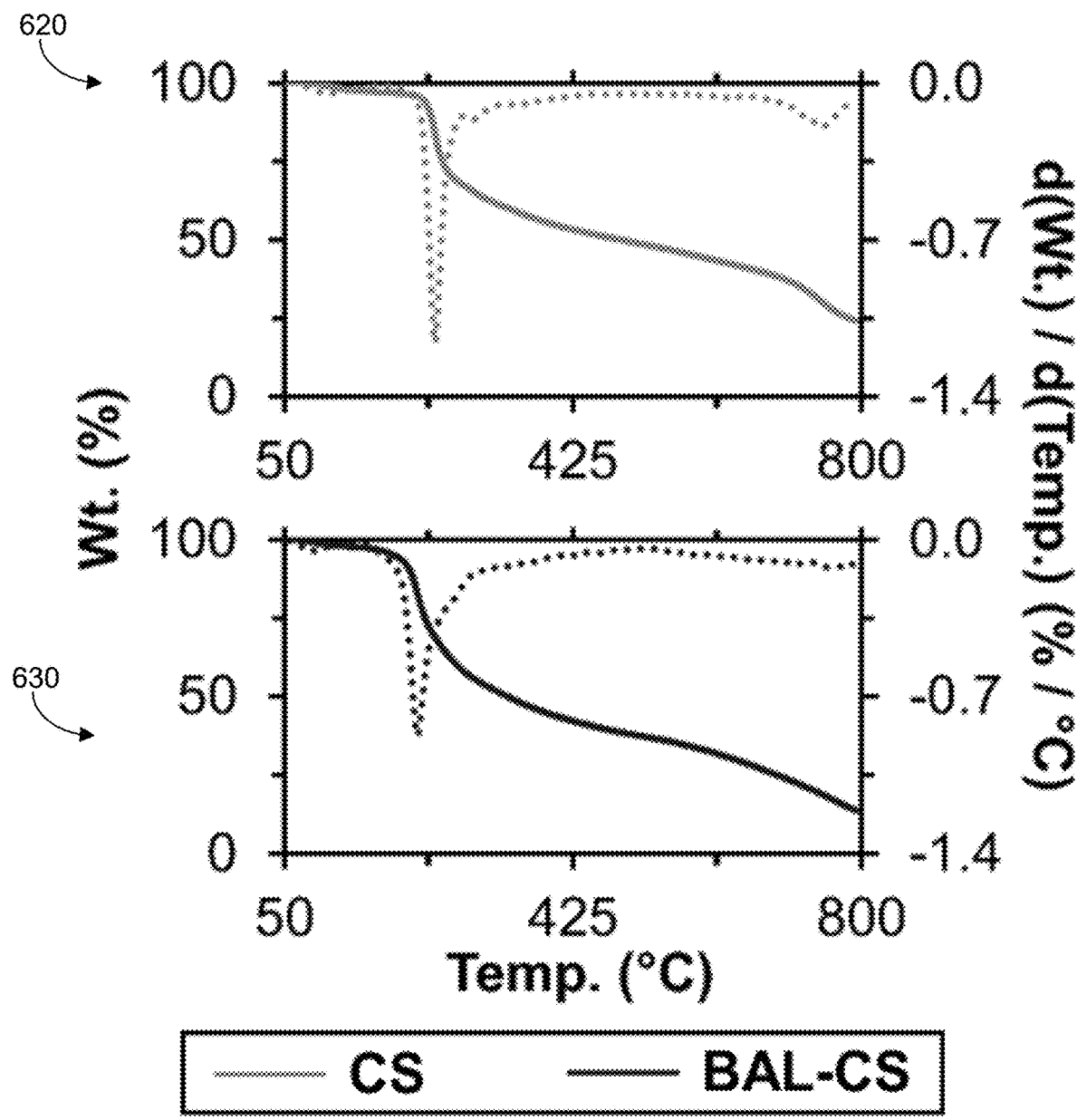
Figure 6C:
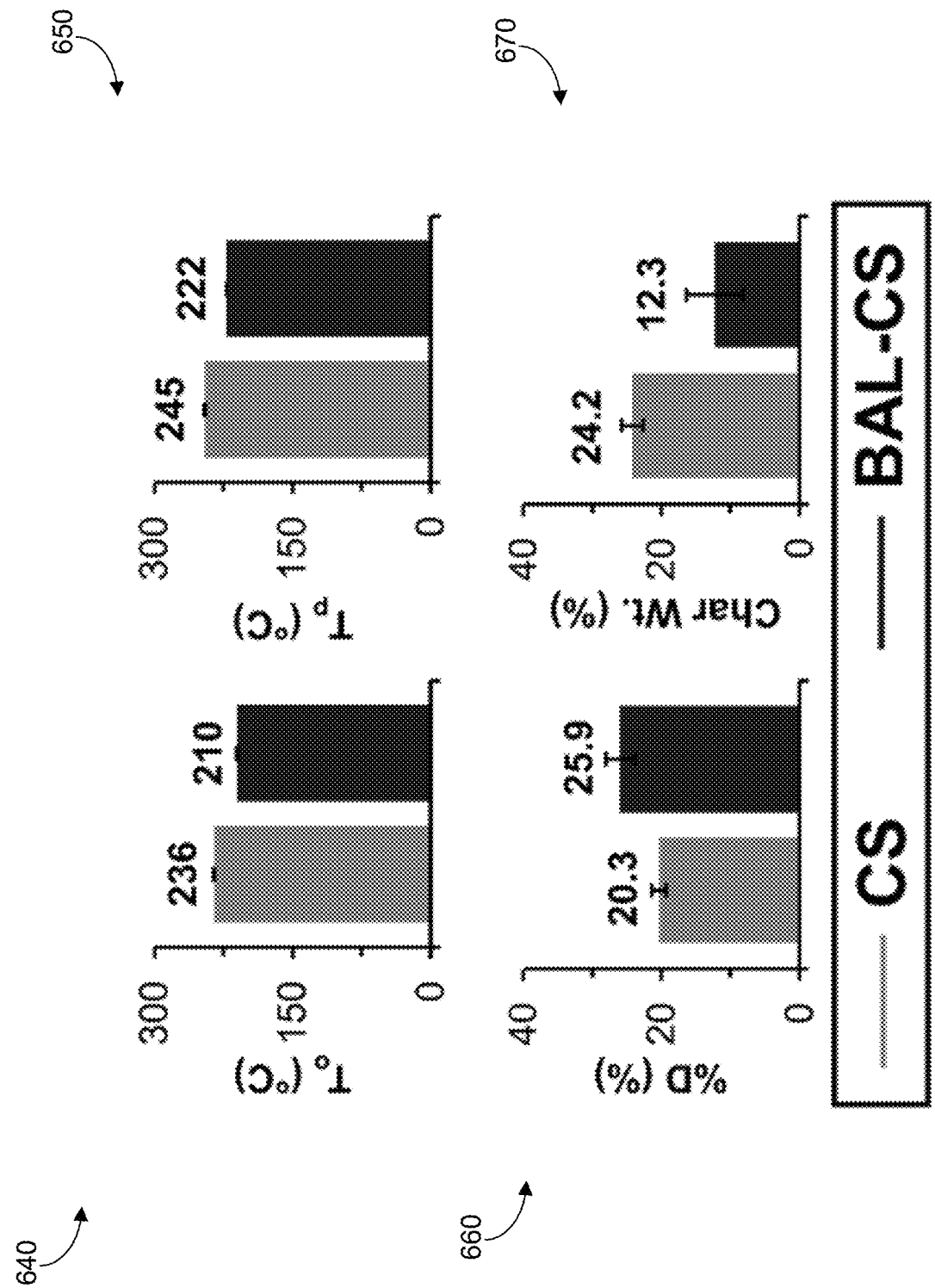
Figure 7:
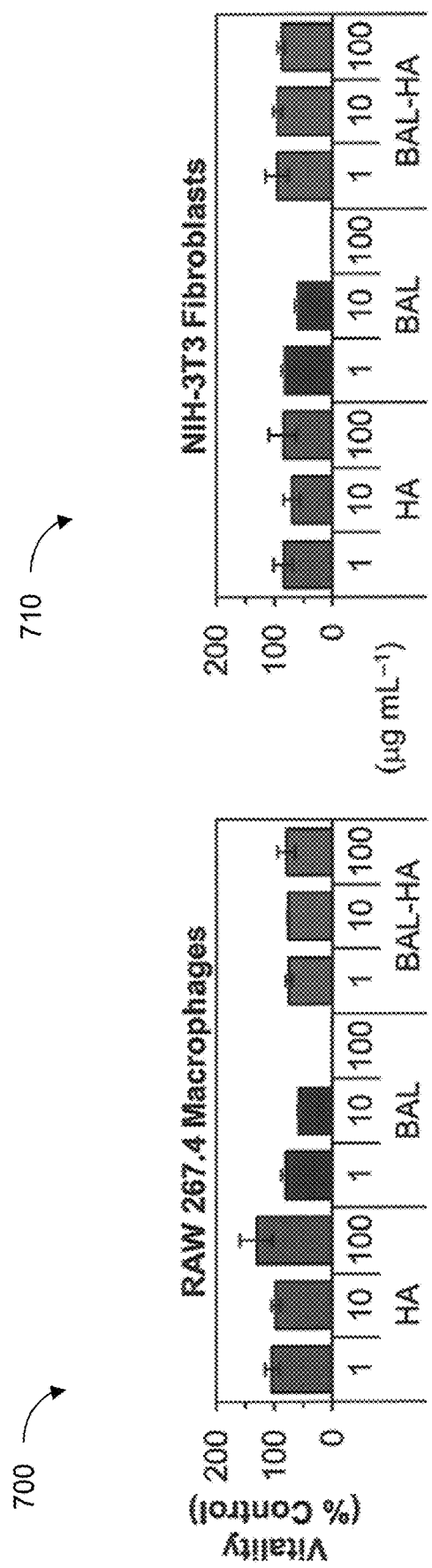
FIG. 7 shows data that illustrates the cytocompatibility of a plurality of compounds.

FIG. 6B shows data representing TGA of CS and BAL-CS. Graphs 620 and 630 show thermograms (solid lines) and the first derivative of the thermograms (dashed lines) of CS (graph 620) and BAL-CS (graph 630). FIG. 6C shows quantitation of the TGA data in graphs 640, 650, 660, and 670. Graph 640 shows data representing $T_o$, which is the onset temperature of the degradation event. Graph 650 shows data representing $T_p$, which is the first derivative peak temperature calculated from the local minima of the first derivative of the degradation curve. Graph 660 shows data representing the weight loss percentage for the degradation event at To. Graph 670 shows the char weight percent is the weight percent remaining at 800° C. The error bars are the sample standard deviation from triplicate runs of CS and BAL-CS BAL-HA Rescues Vitality of Cells Exposed to Cobalt The chelating compound including BAL-HA is capable of rescuing cellular vitality of cells exposed to high levels of cobalt. To show this, the cytocompatibility of HA, BAL, and BAL-HA was quantified using cell enumeration, metabolism, and toxicity assays. FIG. 7 shows graphs 700 and 710 which illustrate the cytocompatibility of a plurality of compounds. HA is cytocompatible, as shown in each of graphs 700 and 710. BAL, however, significantly reduced proliferation in a dose-dependent manner, and at 100 μg mL$^{-1}$ there were hardly any viable cells. Conjugation of BAL to HA rescued BAL-mediated toxicity, as the vitality of BAL-HA was similar to that of control and cells exposed to HA. Labeling the important subcellular structures of nuclei, filamentous actin (F-actin), and mitochondria revealed normal morphologies for NIH-3T3 fibroblasts that were exposed to 10 μg mL$^{-1}$ of HA and BAL-HA. Some cells were observed to associate with aggregates. Fibroblasts exposed to BAL, however, had reduced cortical F-actin structures and disrupted mitochondrial tracks, in agreement with decreased vitality. Cellular vitality was measured using Calcein AM, of macrophages and fibroblasts exposed to HA, BAL, and BAL-HA at the indicated concentrations for 2 days. While at 100 μg mL$^{-1}$ BAL dramatically reduced cellular vitality, BAL-HA remained cytocompatible at the same concentration.

A range of $CoCl_2.6H_2O$ concentrations was examined, and it was determined that 100 μg mL$^{-1}$ would be most appropriate for the in vitro chelation assays since it resulted in a substantially reduced vitality but did not kill all cells, allowing for high sensitivity in assaying for changes in vitality due to chelation. Two types of chelation experiments were conducted. First, a perpetual exposure to $CoCl_2.6H_2O$ and BAL-HA was performed. Second, an acute exposure to $CoCl_2.6H_2O$ was performed, followed by a media change and exposure to BAL-HA for 1 minute, and then followed by a media change to fresh media. Cells perpetually exposed to $CoCl_2.6H_2O$ and BAL-HA still had a significant reduction in vitality compared to control cells. However, there was a dose-dependent increase in vitality with increasing BAL-HA concentration from 0.8-100 mL$^{-1}$. BAL-HA dispersed in cell culture media containing $CoCl_2.6H_2O$ was not stable, likely due to a reduction in the magnitude of BAL-HA that has chelated $Co^{+2}$. The chelation complex would then settle out of solution and smother cells, artificially affecting cellular vitality.

Figure 8:
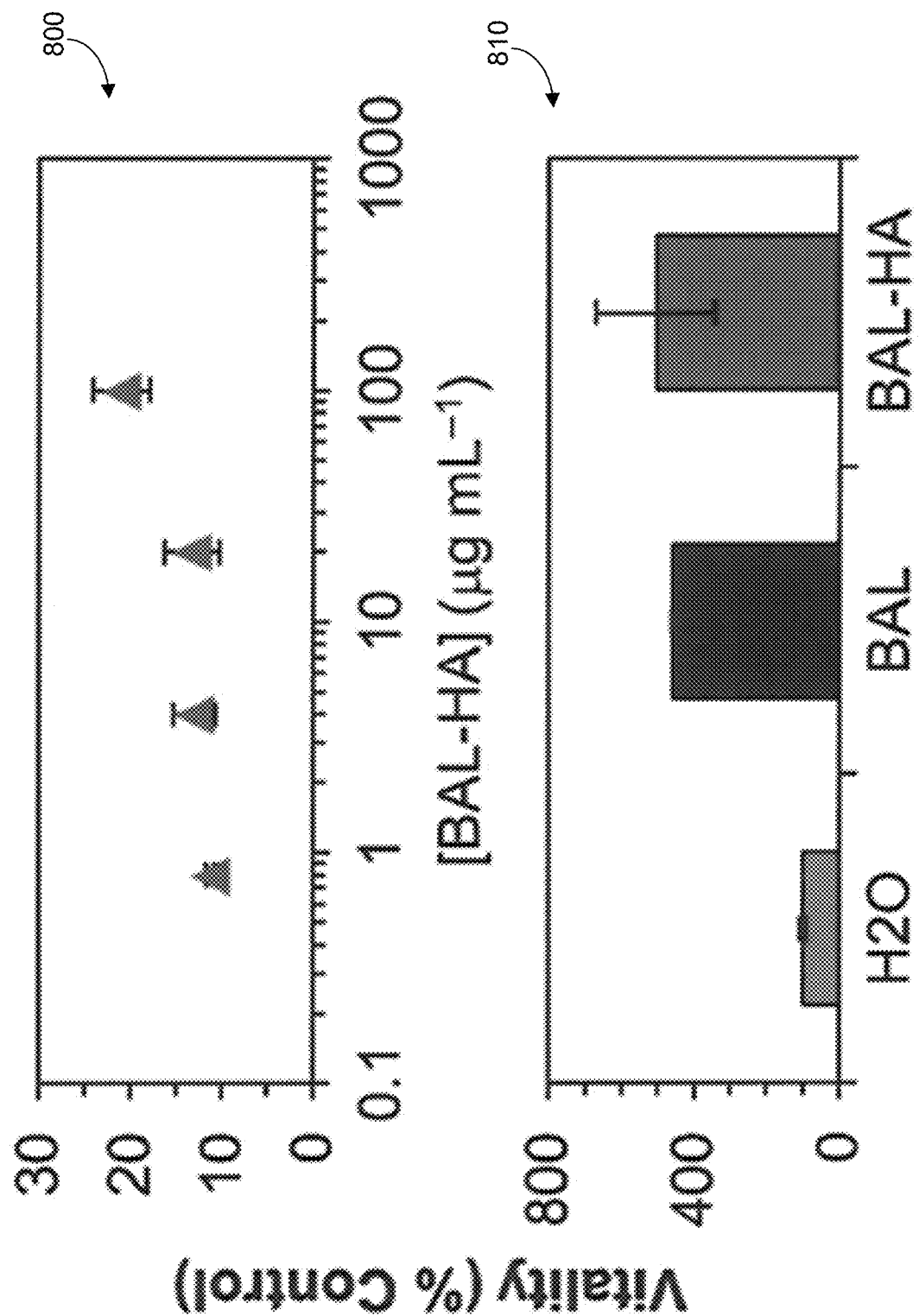
FIG. 8 shows data representing in vitro chelation using BAL-HA.

FIG. 8 shows data representing in vitro chelation using BAL-HA. Graph 800 shows results of RAW 264.7 macrophages exposed to 100 μg mL$^{-1}$ $CoCl_2.6H2O$ and BAL-HA at the indicated concentration for 2 days, after which the cellular vitality was quantified. Graph 810 shows results of RAW 264.7 macrophages exposed to 100 μg mL$^{-1}$ $CoCl_2.6H2O$ for 18 hours. To obtain this data, after exposure, the media was aspirated, and then the cells exposed to 1000 μg mL$^{-1}$ BAL-HA for 1 minute, the BAL-HA solution aspirated, the cells washed with PBS, and then the cells were cultured in fresh media for a day before quantification of cellular vitality. Overall, exposure to BAL-HA rescues cellular vitality.

BAL-HA can be used to treat patients with metal implant-induced metallosis. This includes a minimally invasive surgical procedure, similar to current techniques, that drains the joint cavity of synovial fluid, injects a highly concentrated BAL-HA dispersion that is allowed to incubate in the joint cavity for a brief amount of time, and is then exchanged with fresh synovial fluid mimic. This concept was tested in vitro and demonstrated that BAL-HA could dramatically increase cellular vitality by 500% compared to cells simply receiving a media exchange, as shown in graph 610. These results demonstrate that an exchange of media is not sufficient to rescue vitality and that BAL-HA can have a significant effect in only a brief amount of time in a biological environment. Although BAL also showed improvement in cellular vitality, it is not feasible to inject BAL alone into patients due to its substantial toxicity.

Figure 9:
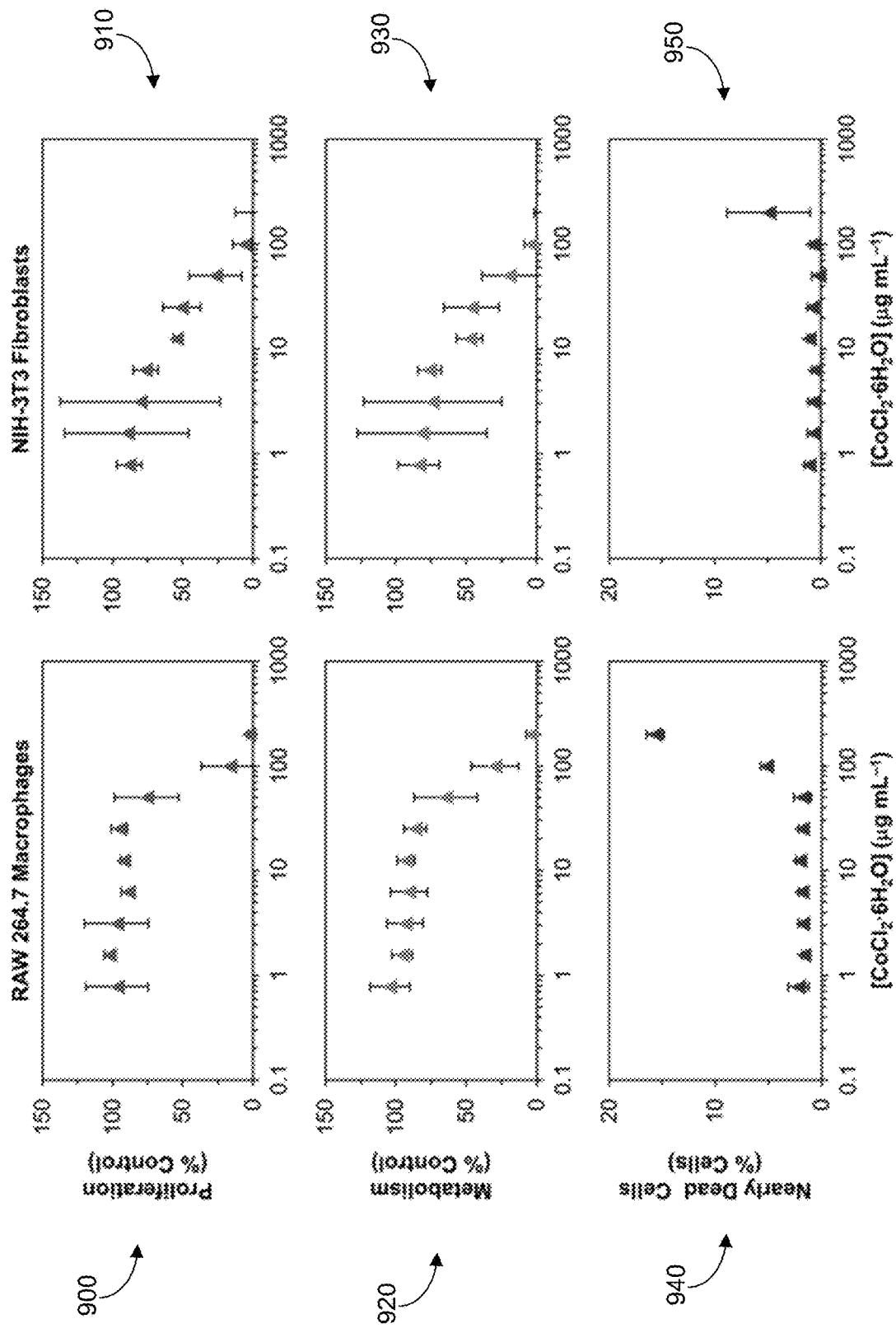
FIG. 9 shows cytocompatibility of cells exposed to varying concentrations of $CoCl_2.6H_2O$.

FIG. 9 shows cytocompatibility of cells exposed to varying concentrations of $CoCl_2.6H_2O$, shown in graphs 900, 910, 920, 930, 940, and 950. The maximal inhibitory concentration is ~50 μg mL$^{-1}$ for RAW 264.7 macrophages and ~25 μg mL$^{-1}$ for NIH-3T3 fibroblasts.

Materials and Methods Synthetic Methods

BAL Functionalized GAGs Preparation: BAL-GAGs were synthesized from either hyaluronic acid sodium salt (Streptococcus equi source, molecular weight ~1.5-1.8 MDa; Sigma-Aldrich, St. Louis, Mo., USA) or chondroitin sulfate A sodium salt (bovine trachea source, Sigma-Aldrich, St. Louis, Mo., USA). The reaction was run by dissolving 150 mg of either HA or CS in deionized (DI) water at 2 mg/mL or 30 mg/mL concentrations, respectively, followed by the addition of 77 mg of (3-Dimethylaminopropyl)-N'-ethylcarbodiimide hydrochloride (EDC) (Oakwood Chemicals, Estill, S.C., USA). The reaction was stirred for 5 minutes before the addition of 46 mg of N-Hydroxysuccinimide (NETS) (Sigma-Aldrich, St. Louis, Mo., USA) and stirred for 5 min. Then, 200 μL of BAL (Alfa Aesar, Ward Hill, Mass., USA) was added and the reaction was stirred for 1.5 hours. The reaction was transferred to dialysis tubing (SnakeSkin™ dialysis tubing; Thermo Scientific, Waltham, Mass., USA) and dialyzed against DI water overnight, frozen to −80° C., and lyophilized to dryness.

Material Characterization

Proton Nuclear Magnetic Resonance ($^1$H NMR) Spectroscopy: $^1$H NMR spectroscopy was performed on a 300 MHz NMR instrument (Bruker Avance™ 300) in deuterated water.

Fourier Transform Infrared (FTIR) Spectroscopy: FTIR spectroscopy was performed using a Perkin Elmer Frontier FT-IR Spectrometer with an attenuated total reflectance attachment containing a germanium crystal. Raw spectra were obtained over a range of 4000-700 cm$^{-1}$ with 4 cm$^{-1}$ resolution and 4 accumulations. All spectra were converted from percent transmittance to absorbance and normalized via the hydroxyl stretch at ~3500 cm$^{-1}$, converted back to percent transmittance, and then offset for clarity. Normalized FTIR spectra were truncated from 1750-1500 cm$^{-1}$ and converted to absorbance. Fityk (Version 0.9.8) was used to baseline subtract all spectra and "deconvolute" carbonyl peaks.

Thermogravimetric Analysis (TGA): A PerkinElmer TOA 4000 was used to perform TGA from 50-800° C. with a ramp rate of 10° C. min$^{-1}$ under $N_2$. The raw data was analyzed using TRIOS software (TA Instruments).

Dynamic Light Scattering (DLS): A Zetasizer Nano ZS (Malvern Instruments Ltd., Worcestershire, UK) was used to perform DLS on samples dispersed in DI water (1 mg/mL). Three measurements consisting of 10 scans at 10 seconds per scan were acquired in backscatter) (173°) mode.

Zeta Potential: A Zetasizer Nano ZS (Malvern Instruments Ltd., Worcestershire, UK) was used to perform zeta potential on samples dissolved in DI water (1 mg/mL) using Malvern disposable folded capillary cells. Three measurements consisting of at least 10 scans at 10 seconds per scan were acquired.

Absorbance Spectroscopy: A Varian Cary 5000 spectrophotometer (Agilent Technologies, Santa Clara, Calif.) was used to perform absorbance spectroscopy from 300-800 nm with a 1 nm step size. Samples were measured in a 10 mm path length Infrasil® quartz cell (Starna Cells, Inc., Atascadero, Calif.).

Ellman's Assay: Thiol quantification was determined using a modified Ellman's test protocol previously reported. A stock solution of Ellman's reagent was prepared using 5,5-dithio-bis-(2-nitrobenzoic acid) (Alfa Aesar, Ward Hill, Mass., USA) and sodium acetate (Sigma-Aldrich, St. Louis, Mo., USA) in DI water with a final concentration of 2 mM and 50 mM, respectively. A 1 M Tris buffer (Promega Corporation, Madison, Wis., USA) solution was prepared in DI water and adjusted to pH 8.0. Samples were analyzed by mixing 10.1 µL of Ellman's reagent, 20.2 µL of Tris buffer, 169.7 µL DI water, and 100 µL of sample into an ultraviolet (UV)-transparent 96 well plate. Samples were mixed, incubated at room temperature, and read on microplate reader (Tecan Safire2™) at 412 nm.

Chelation Characterization

Qualitative Chelation: The samples were prepared using 4 mg of either HA or BAL-HA dissolved in 3 mL DI water. Each sample was spiked with either 1 mL DI water or 1 mM stock solutions of $CoCl_2.6H_2O$ (VWR Life Sciences, Radnor, Pa., USA), $NiCl_2.6H_2O$ (Alfa Aesar, Ward Hill, Mass., USA), $CrCl_3.6H_2O$ (Alfa Aesar, Ward Hill, Mass., USA), and $CrO_3$ (Alfa Aesar, Ward Hill, Mass., USA) and imaged immediately. Samples were dialyzed against DI water for 5 days (dialysis water was changed once a day) and removed for imaging. Then, samples were frozen to −80° C., lyophilized to dryness, and imaged.

Cobalt Absorption Titration: A 1 mg/mL solution of BAL-HA was prepared (481.9 mg in DI water) and titrated at room temperature and constant stirring with 100 mM $CoCl_2.6H_2O$. Aliquots were analyzed after each 200 µL addition of cobalt via absorbance spectroscopy from 300-800 nm.

Cell Culture and Bioassays

Cell Culture: NIH-3T3 murine fibroblasts were cultured in Dulbecco's modified Eagle Medium (DMEM) containing 4500 mg L$^{-1}$ D-glucose, 584 mg L$^{-1}$ L-glutamine, and 100 mg L$^{-1}$ sodium pyruvate (#11995040, ThermoFisher Scientific), supplemented with newborn calf serum (#16010159, ThermoFisher Scientific) at 10% v/v, and penicillin-streptomycin (#15140122, ThermoFisher Scientific) diluted to 100 U mL$^{-1}$. RAW 264.7 murine macrophages were cultured in the same DMEM with penicillin-streptomycin but with fetal bovine serum (#26140079, ThermoFisher Scientific). Cells were maintained at 37° C. in a humidified, 5% $CO_2$ atmosphere. For all experiments, NIH-3T3 fibroblasts were seeded at 3×10$^4$ cells cm$^{-2}$ and RAW 264.7 macrophages were seeded at 2×10$^4$ cells cm$^{-2}$.

Cellular Vitality: For vitality analysis, cells were cultured in 96-well plates, and when time for vitality analysis, the cell media was aspirated. The cells were washed with phosphate buffered saline (PBS). The cells were exposed to the staining solution for 15 minutes before fluorometric analysis. Cellular enumeration was performed by exposing cells to 20 µM of the cell-permeable Hoechst 33342 (#62249, ThermoFisher Scientific) that labels all cellular nuclei. Cellular metabolism was quantified by exposing cells to 5 µM of Calcein AM (PromoCell, Inc. #CA707-80011-2, VWR) that becomes fluorescent upon intracellular esterase conversion. Late apoptotic and necrotic cells were labeled with 2.5 µM of ethidium homodimer 1 (#L3224, ThermoFisher Scientific). Fluorescence intensity was quantified on a microplate reader (Tecan Safire2™) with excitations of 350/20 nm, 483/20 nm, and 528/20 nm and emissions of 461/20 nm, 525/20 nm, and 617/20 nm for Hoechst 33342, Calcein AM, and ethidium homodimer-1, respectively. To confirm the bulk measurements, fluorescence imaging was performed using an EVOS FL Auto Cell Imaging System (ThermoFisher Scientific), using the system's automation to acquire multiple fields of view per well and automatically stitch them together into one large image.

Sub-cellular Compartment Imaging: Cells were cultured on sterile #1.5 coverslips (22 mm×22 mm) in 35 mm dishes. After 1 day of exposure to the experimental conditions, the cells were exposed to 20 µM of Hoechst 33342 and 1 µM of MitoTracker® Red CMXRos (#M7512, ThermoFisher Scientific) for 30 min in cell culture media. The cells were washed three times with PBS and then exposed to 0.2% Triton X-100 for 5 minutes. The cells were washed three more times in PBS and then exposed to 100 nM of Acti-Stain™ 488 phalloidin (#PHDG1, Cytoskeleton, Inc.) for 1 hour. After three more washes with PBS, the coverslips were mounted onto microscopy slides with mounting medium (SouthernBiotech Fluoromount-G™, #OB100-01, ThermoFisher Scientific). Sub-cellular imaging was performed on an EVOS FL Auto Cell Imaging System (ThermoFisher Scientific) with a 100×, 1.4 numerical aperture, oil-immersion objective.

$CoCl_2.6H_2O$ Standard Curve: A 5 mg mL$^{-1}$ solution of $CoCl_2.6H_2O$ in water was sterilized by exposure to ultraviolet light for 5 minutes and was then aseptically diluted to 200 µg mL$^{-1}$ with complete cell culture media. Then, a 2-fold serial dilution using complete cell culture media was performed until reaching the last concentration of 0.781 µg mL$^{-1}$. The cells' medias were then aspirated and replaced as indicated with these CoCl$_2$.6H$_2$O-laden medias in technical triplicates. The cells were cultured for 2 days and then assayed for cytocompatibility.

In Vitro Chelation: Two types of experiments were performed: perpetual and acute exposure to the chelator. For perpetual exposure, cells were seeded in 96-well plates, incubated for 6 hours, and then exposed to 100 µg mL$^{-1}$ of CoCl$_2$.6H$_2$O and varying concentrations of BAL-HA for 2 days followed by vitality analysis. For acute exposure, cells were seeded in 96-well plates, incubated for 6 hours, and then exposed to 100 µg mL$^{-1}$ of CoCl$_2$.6H$_2$O for 18 hours. Cobalt-laden medias were aspirated, and the cells were exposed to DI water only, 1 mg mL$^{-1}$ BAL in DI water, or 1 mg mL$^{-1}$ BAL-HA in DI water for 1 minute. The wells were washed with PBS, fresh media was added, and the cells were cultured another day before cytocompatibility analysis.

A number of embodiments have been described. Nevertheless, it will be understood that various modifications may be made without departing from the spirit and scope of the data processing system described herein. Accordingly, other embodiments are within the scope of the following claims.

What is claimed is:

1. A compound, comprising a polysaccharide moiety covalently coupled to one or more chelating agents comprising British anti-Lewisite (BAL), wherein the polysaccharide moiety comprises a glycosaminoglycan moiety, and wherein the one or more chelating agents functionalize a carboxylic acid functional group of the glycosaminoglycan moiety to form a metal-chelating polymeric system that removes metals from a fluid.

2. The compound of claim 1, wherein the one or more chelating agents are covalently bonded to the polysaccharide moiety.

3. The compound of claim 1, wherein each of the one or more chelating agents is independently a chelator of one or more metals selected from the group consisting of As, Hg, Au, Pb, Co, Ni, Cr, Ti, Ta, Cu, Fe, Mo, and Gd.

4. The compound of claim 1, wherein each of the one or more chelating agents is independently a chelator of one or more metals selected from the group consisting of Co, Ni, and Cr.

5. The compound of claim 1, wherein each of the one or more chelating agents are the same.

6. The compound of claim 1, wherein the chelating agent is dimercaprol.

7. The compound of claim 1, wherein the glycosaminoglycan moiety is selected from the group consisting of a hyaluronic acid polymer and a sulfated glycosaminoglycan moiety.

8. The compound of claim 1, wherein the glycosaminoglycan moiety is a hyaluronic acid polymer.

9. The compound of claim 8, wherein the compound comprises about 1:1 to about 1:3 chelator to repeat unit of the hyaluronic acid polymer.

10. The compound of claim 8, wherein the compound comprises about 1:1 chelator to repeat unit of the hyaluronic acid polymer.

11. The compound of claim 1, wherein the glycosaminoglycan moiety is a sulfated glycosaminoglycan moiety.

12. The compound of claim 11, wherein the glycosaminoglycan moiety is chondroitin sulfate.

13. The compound of claim 12, wherein the compound comprises about 1:1 to about 1:3 chelator to repeat unit of the chondroitin sulfate.

14. The compound of claim 12, wherein the compound comprises about 1:1 chelator to repeat unit of the chondroitin sulfate.

15. The compound of claim 1 wherein the glycosaminoglycan moiety is hyaluronic acid and the chelating agent is dimercaprol.

16. A pharmaceutical composition, comprising the compound of claim 1, and a pharmaceutically acceptable carrier.

17. The pharmaceutical composition of claim 16, wherein the pharmaceutically acceptable carrier comprises water.

18. The pharmaceutical composition of claim 16, wherein the composition is formulated as an injectable hydrogel.

19. The compound of claim 1, wherein a chelation efficiency of the one or more chelating agents exceeds 10 micrograms of metal per milligram of the compound.

* * * * *

UNITED STATES PATENT AND TRADEMARK OFFICE
CERTIFICATE OF CORRECTION

| | |
|---|---|
| PATENT NO. | : 11,479,617 B2 |
| APPLICATION NO. | : 16/552774 |
| DATED | : October 25, 2022 |
| INVENTOR(S) | : Stefanie A. Sydlik et al. |

It is certified that error appears in the above-identified patent and that said Letters Patent is hereby corrected as shown below:

On the Title Page

Column 2, Line 7, Item (56) delete "top" and insert -- hip --

Column 2, Line 14, Item (56) delete "Impianted" and insert -- Implanted --

Column 2, Line 24, Item (56) delete "Pharmacuetical" and insert -- Pharmaceutical --

Signed and Sealed this
Thirty-first Day of January, 2023

Katherine Kelly Vidal
*Director of the United States Patent and Trademark Office*